(12) United States Patent
Tian et al.

(10) Patent No.: US 8,403,904 B2
(45) Date of Patent: Mar. 26, 2013

(54) SUPERABSORBENT POLYMER HAVING A CAPACITY INCREASE

(71) Applicant: Evonik Stockhausen, LLC, Greensboro, NC (US)

(72) Inventors: Gonglu Tian, Greensboro, NC (US); David L. Bergman, Jr., Greensboro, NC (US); Yaru Shi, Greensboro, NC (US)

(73) Assignee: Evonik Stockhausen, LLC, Greensboro, NC (US)

( * ) Notice: Subject to any disclaimer, the term of this patent is extended or adjusted under 35 U.S.C. 154(b) by 0 days.

(21) Appl. No.: 13/644,515

(22) Filed: Oct. 4, 2012

(65) Prior Publication Data

US 2013/0045377 A1    Feb. 21, 2013

Related U.S. Application Data

(62) Division of application No. 12/775,984, filed on May 7, 2010, now Pat. No. 8,304,369.

(51) Int. Cl.
*A61F 13/20* (2006.01)

(52) U.S. Cl. ............ 604/385.23; 604/367; 502/402; 525/329.5; 525/327.4

(58) Field of Classification Search ............ 604/367, 604/385.23; 502/402; 525/329.5
See application file for complete search history.

(56) References Cited

U.S. PATENT DOCUMENTS

| | | | |
|---|---|---|---|
| 2,985,631 A | 5/1961 | Jones et al. | |
| 3,423,376 A | 1/1969 | Gobran et al. | |
| 4,755,560 A | 7/1988 | Ito et al. | |
| 4,988,345 A | 1/1991 | Reising | |
| 6,716,929 B2 | 4/2004 | Wilson | |
| 6,998,367 B2 | 2/2006 | Qin | |
| 7,073,373 B2 | 7/2006 | La Fortune | |
| 7,285,614 B2 | 10/2007 | Jonas et al. | |
| 2007/0135554 A1 | 6/2007 | McIntosh et al. | |
| 2007/0265405 A1 | 11/2007 | Lang et al. | |
| 2008/0140037 A1 | 6/2008 | Newman | |
| 2008/0200614 A1 | 8/2008 | Yang et al. | |
| 2008/0234420 A1 | 9/2008 | Smith et al. | |
| 2009/0191408 A1 | 7/2009 | Tian et al. | |
| 2010/0069551 A1 | 3/2010 | Minge et al. | |
| 2010/0099781 A1 | 4/2010 | Tian et al. | |
| 2010/0130355 A1 | 5/2010 | Tian et al. | |
| 2011/0121231 A1 | 5/2011 | Tian et al. | |

FOREIGN PATENT DOCUMENTS

| | | |
|---|---|---|
| DE | 102006054158 A1 | 5/2008 |
| EP | 1486516 A2 | 12/2004 |
| GB | 2453669 A | 4/2009 |
| WO | 0242344 A2 | 5/2002 |

OTHER PUBLICATIONS

International Search Report mailed on Jul. 5, 2011 in PCT/US2011/034504.

(Continued)

*Primary Examiner* — Colleen Dunn
*Assistant Examiner* — Haytham Soliman
(74) *Attorney, Agent, or Firm* — Smith Moore Leatherwood LLP; Philip P. McCann

(57) ABSTRACT

The present invention relates to a particulate superabsorbent polymer comprising a monomer and an internal crosslinker agent wherein the particulate superabsorbent polymer has a Centrifuge Retention Capacity Increase of 2 g/g or more as set forth herein in the Centrifuge Retention Capacity Increase Test. The present invention further relates to a superabsorbent polymer comprising an internal crosslinker agent comprising a silane compound comprising at least one vinyl group or one allyl group attached to a silicon atom, and at least one Si—O bond. The present invention further relates to an absorbent article that includes such particulate superabsorbent polymers.

8 Claims, 8 Drawing Sheets

OTHER PUBLICATIONS

Shi et al., U.S. Appl. No. 13/091,844, filed Apr. 21, 2011.
Smith et al., U.S. Appl. No. 13/524,232, filed Jun. 15, 2012.
Tian et al., Gulf Cooperation Council Application No. 2011/18337, filed May 4, 2011.
Tian et al., U.S. Appl. No. 13/564,810, filed Aug. 2, 2012.
Written Opinion mailed on Jul. 5, 2011 in PCT/US2011/034504.

SUPERABSORBENT POLYMER HAVING A CAPACITY INCREASE

This is a divisional application of U.S. application Ser. No. 12/775,984 filed May 7, 2010, currently pending, the disclosure of which is expressly incorporated herein by reference.

BACKGROUND

The present invention is directed towards a superabsorbent polymer. A superabsorbent polymer is a crosslinked partially neutralized polymer, including crosslinked polyacrylic acids or crosslinked starch-acrylic acid graft polymers, that is capable of absorbing large amounts of aqueous liquids and body fluids, such as urine or blood, with swelling and the formation of hydrogels, and of retaining the aqueous liquids under a certain pressure in accordance with the general definition of superabsorbent polymer. Superabsorbent polymer may be formed into particles, generally referred to as particulate superabsorbent polymer, wherein the particulate superabsorbent polymer may be post-treated with surface crosslinking, surface treatment, and other treatment to form particulate superabsorbent polymer compositions. The acronym SAP may be used in place of superabsorbent polymer, superabsorbent polymer composition, and particles hereof. A primary use of superabsorbent polymer and superabsorbent polymer compositions is in sanitary articles, such as babies' diapers, incontinence products, or sanitary towels. A comprehensive survey of superabsorbent polymers, and their use and manufacture, is given in F. L. Buchholz and A. T. Graham (editors) in "Modern Superabsorbent Polymer Technology," Wiley-VCR, New York, 1998.

Superabsorbent polymers may be prepared by initially polymerizing unsaturated carboxylic acids or derivatives thereof, such as acrylic acid, alkali metal (e.g., sodium and/or potassium) or ammonium salts of acrylic acid, alkyl acrylates, and the like in the presence of relatively small amounts of an internal crosslinker such as a di- or poly-functional monomers that may include N,N'-methylenebisacrylamide, trimethylolpropane triacrylate, ethylene glycol di(meth)acrylate, or triallylamine. The di- or poly-functional monomer materials may serve as covalent internal crosslinking agents to lightly crosslink the polymer chains, thereby rendering them water-insoluble, yet water-swellable. These lightly crosslinked superabsorbent polymers contain a multiplicity of carboxyl groups attached to the polymer backbone. These carboxyl groups generate an osmotic driving force for the absorption of body fluids by the crosslinked polymer network.

In addition to covalent internal crosslinking agents, ionic internal crosslinking agents have been utilized to prepare superabsorbent polymers as well. The ionic internal crosslinking agents are generally coordination compounds comprising polyvalent metal cations, such as $Al^{3+}$ and $Ca^{2+}$, as disclosed in U.S. Pat. No. 6,716,929 and U.S. Pat. No. 7,285,614. The superabsorbent polymers disclosed in these patents have a slow rate of absorption, due to the presence of ionic crosslinks. In this context, slow rate may be measured by the Vortex Test and slow rate SAPs generally have a vortex time of 180 sec or more.

Superabsorbent polymers, useful as absorbents in absorbent articles such as disposable diapers, need to have adequately high sorption capacity, as well as adequately high gel strength. Sorption capacity needs to be sufficiently high to enable the absorbent polymer to absorb significant amounts of the aqueous body fluids encountered during use of the absorbent article. Gel strength relates to the tendency of the swollen polymer particles to deform under an applied stress, and needs to be such that the particles do not deform and fill the capillary void spaces in the absorbent member or article to an unacceptable degree, so-called gel blocking, thereby inhibiting the rate of fluid uptake or the fluid distribution by the member or article. Once gel-blocking occurs, it can substantially impede the distribution of fluids to relatively dry zones or regions in the absorbent article and leakage from the absorbent article can take place well before the particles of absorbent polymer in the absorbent article are fully saturated or before the fluid can diffuse or wick past the "blocking" particles into the rest of the absorbent article.

Another property of these particulate superabsorbent polymers is what is called gel bed permeability. Gel permeability of particulate superabsorbent polymer composition is a measure of how rapidly liquid flows through the mass of swollen particles. In general, the gel permeability of a zone, or layer, comprising swollen particulate superabsorbent polymer can be increased by increasing the cross link density of the polymer gel, thereby increasing the gel strength. Particulate superabsorbent polymers with relatively high gel permeability can be made by increasing the level of internal crosslinking, which increases the strength of the swollen gel, but this typically also reduces the absorbent capacity of the gel undesirably, as described above.

In the past decade, significant investments have been made to improve the performance of such SAP's, e.g. to provide a higher absorbent capacity per volume, to improve fluid distribution throughout the SAP's, and to reduce so-called gel blocking of the SAP's. One area of focus has been to modify the surface of SAP particles such that optimum gel permeability is achieved without significantly compromising the absorbent capacity.

The current trend in absorbent articles including diapers, is toward ever thinner core constructions having a reduced or zero cellulose fiber, or fluff, content and an increased SAP content. As diaper cores become thinner, the SAP particles must possess properties that historically have been supplied by fluff pulp. Since reducing the fiber content between the superabsorbent polymers increases the risk of gel blocking, there is a need to provide thinner cores without much or any fibers, which do not suffer from gel blocking.

Hence, there is still a need to improve the absorbent capacity and gel strength of particulate superabsorbent polymer at the same time.

SUMMARY

The present invention includes numerous embodiments, of which some are included herein. One embodiment of the present invention is a particulate superabsorbent polymer comprising a monomer and a crosslinker composition comprising an internal crosslinking agent wherein the particulate superabsorbent polymer has a Centrifuge Retention Capacity Increase (CRCI) of 2 g/g or more, from 2 g/g to about 50 g/g, from 2 g/g to about 40 g/g, from about 3 g/g to about 30 g/g, or from about 3 g/g to about 15 g/g, as set forth herein in the Centrifuge Retention Capacity Increase Test.

Another embodiment of the present invention includes a superabsorbent polymer including an internal crosslinker composition which contains a silane compound comprising at least one vinyl group or allyl group directly attached to a silicon atom and at least one Si—O bond. The silane compound may be selected from one of the following:

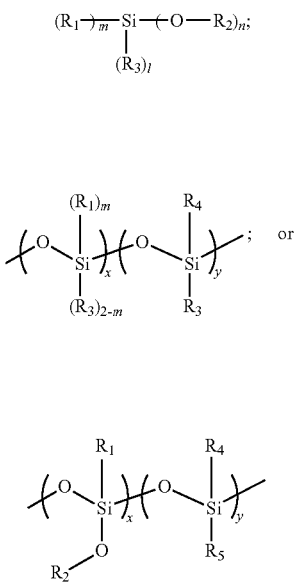

wherein
$R_1$ represents $C_2$ to $C_3$ alkenyl,
$R_2$ represents H, $C_1$ to $C_4$ alkyl, $C_2$ to $C_5$ alkenyl, $C_6$ to $C_8$ aryl, $C_2$ to $C_5$ carbonyl,
$R_3$ represents H, $C_1$ to $C_4$ alkyl, $C_6$ to $C_8$ aryl,
$R_4$ and $R_5$ independently represent H, $C_1$ to $C_4$ alkyl, $C_6$ to $C_8$ aryl,
m represents an integer of from 1 to 3, preferably 1 to 2,
n represents an integer of from 1 to 3, preferably 2 to 3,
l represents an integer of from 0 to 2, preferably 0 to 1,
m+n+1=4,
x represents an integer larger than 1, and
y represents an integer of 0 or larger than 0.

In one aspect, the silane compound may be selected from vinyltriisopropenoxy silane, vinyltriacetoxysilane, vinyltrimethoxysilane, vinyltriethoxysilane, diethoxymethylvinyl silane, and polysiloxane comprising at least two vinyl groups.

In a further aspect, the superabsorbent polymer of the present invention may further comprise a second internal crosslinker. The second internal crosslinker may be selected from the group polyethylene glycol monoallyl ether acrylate, ethoxylated trimethylol propane triacrylate, and polyethylene glycol diacrylate.

Another embodiment of the current invention is a superabsorbent polymer composition comprising a superabsorbent polymer comprising at least one monomer, an internal crosslinking composition containing a silane compound comprising at least one vinyl group or allyl group directly attached to a silicon atom and at least one Si—O bond, a salt forming cation, and a surface crosslinking agent wherein the monomer is selected from an ethylenically unsaturated carboxylic acid, ethylenically unsaturated carboxylic acid anhydride, salts or derivatives thereof based on the superabsorbent polymer. In another aspect, the internal crosslinking composition is from about 0.001% by weight to about 5% by weight based on the monomer Another embodiment of the current invention is a method to make a superabsorbent polymer composition wherein the method comprises the steps of preparing a superabsorbent polymer, polymerizing the components of the superabsorbent polymer into a hydrogel, preparing particulate superabsorbent polymer, surface treating the particulate superabsorbent polymer to make particulate superabsorbent polymer composition. Numerous other aspects of embodiments, features, and advantages of the present invention will appear from the following detailed description, accompanying drawings, and claims. In the interest of brevity and conciseness, any ranges of values set forth in this specification contemplate all values within the range and are to be construed as support for claims reciting any sub-ranges having endpoints which are real number values within the specified range in question.

These and other aspects, advantages, and salient features of the present invention will become apparent from the following detailed description, the accompanying drawings, and the appended claims.

BRIEF DESCRIPTION OF THE FIGURES

The foregoing and other features, aspects, and advantages of the present invention will become better understood with regard to the following description, appended claims, and accompanying drawings where.

DEFINITIONS

Figure 1:
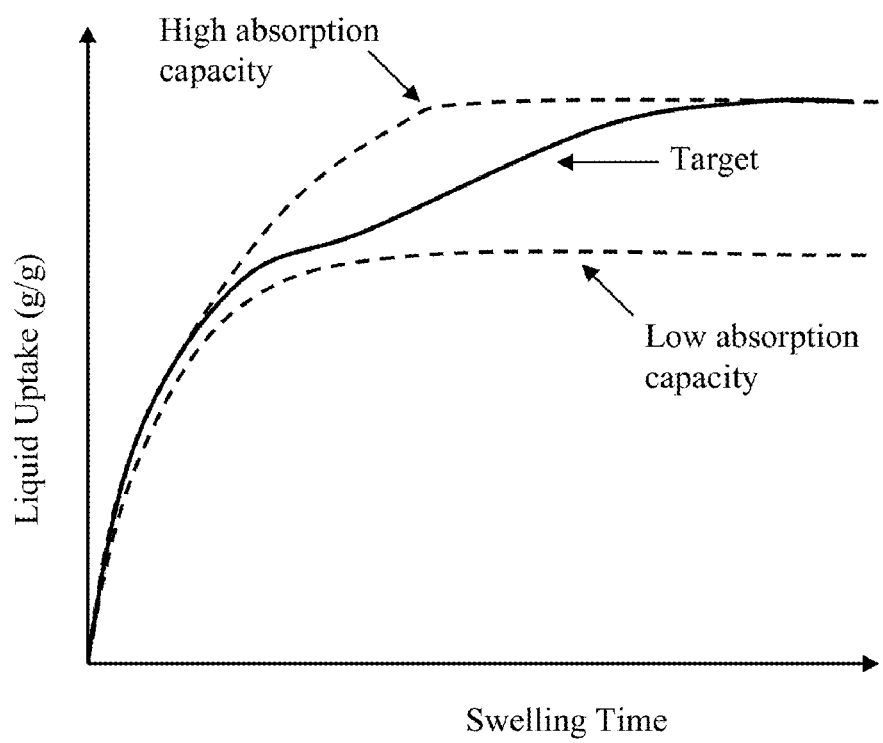
FIG. 1 is a graph showing an increase of absorption capacity over time.

It should be noted that, when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The term "absorbent article" as used herein refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products, breast pads, care mats, bibs, wound dressing products, and the like. Absorbent articles may further include floor cleaning articles, food industry articles, and the like. As used herein, the term "body fluids" or "body exudates" includes, but is not limited to, urine, blood, vaginal discharges, breast milk, sweat and fecal matter.

The term "Centrifuge Retention Capacity (CRC)" as used herein refers to the ability of the particulate superabsorbent polymer to retain liquid therein after being saturated and subjected to centrifugation under controlled conditions and is stated as grams of liquid retained per gram weight of the sample (g/g). CRC testing may be conducted at an assigned testing temperature for an assigned period of testing time, noted as CRC (testing temperature, testing time). As used herein, the term "testing temperature" refers to the temperature of the test solution in which the sample of particulate superabsorbent polymer is wetted. The term "testing time" refers to the time period that the sample of particulate superabsorbent polymer is wetted in a test solution. For example, CRC(rt, 0.5 hr) refers to a CRC with a testing temperature of room temperature (rt, about 23° C.) and a testing time of 0.5 hour.

The term "Centrifuge Retention Capacity Increase (CRCI)" or "CRC Increase" or "Capacity Increase" is defined as the increase in the CRC that occurs and is calculated as the difference between a second CRC and a first CRC. As used herein, the term "first CRC" or "initial CRC" generally refers to CRC(rt, 0.5 hr), although another CRC value may be used. The "second CRC" may be tested at room temperature or higher, preferably from about 23° C. to about 50° C., for at least about 1 hour, preferably from about 2 hours to 24 hours. The CRC Increase is measured according to the CRC Increase Test Method described hereinbelow.

The term "Centrifuge Retention Capacity Increase Rate" or "CRCIR" as used herein refers to the CRC increase per hour (g/g/hour) and is measured according to the Centrifuge Retention Capacity Increase Rate Test Method described hereinbelow The terms "crosslinked", "crosslink", "crosslinker", or "crosslinking" as used herein refers to any means for effectively rendering normally water-soluble materials substantially water-insoluble but swellable. Such a crosslinking means can include, for example, physical entanglement, crystalline domains, covalent bonds, ionic complexes and associations, hydrophilic associations such as hydrogen bonding, hydrophobic associations, or Van der Waals forces.

The term "internal crosslinker" as used herein refers to use of a crosslinker in the monomer solution to form the polymer.

The term "Darcy" is a CGS unit of permeability. One Darcy is the permeability of a solid through which one cubic centimeter of fluid, having a viscosity of one centipoise, will flow in one second through a section one centimeter thick and one square centimeter in cross-section, if the pressure difference between the two sides of the solid is one atmosphere. It turns out that permeability has the same units as area; since there is no SI unit of permeability, square meters are used. One Darcy is equal to about $0.98692 \times 10^{-12}$ m$^2$ or about $0.98692 \times 10^{-8}$ cm$^2$.

The term "diaper" as used herein refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

The term "disposable" as used herein refers to absorbent articles that are not intended to be laundered or otherwise restored or reused as an absorbent article after a single use. Examples of such disposable absorbent articles include, but are not limited to, personal care absorbent articles, health/medical absorbent articles, and household/industrial absorbent articles.

The term "dry superabsorbent polymer composition" as used herein generally refers to the superabsorbent polymer composition having less than about 10% moisture.

The term "hydrolysable bonds" as used herein refers to bonds that can be broken by coming in contact with water, such as anhydrous bonds.

The term "mass median particle size" of a given sample of particles of superabsorbent polymer composition is defined as the particle size, which divides the sample in half on a mass basis, i.e., half of the sample by weight has a particle size greater than the mass median particle size, and half of the sample by mass has a particle size less than the mass median particle size. Thus, for example, the mass median particle size of a sample of superabsorbent polymer composition particles is 2 microns if one-half of the sample by weight is measured as more than 2 microns.

The terms "particle," "particulate," and the like, when used with the term "superabsorbent polymer," refer to the form of discrete units. The units can comprise flakes, fibers, agglomerates, granules, powders, spheres, pulverized materials, or the like, as well as combinations thereof. The particles can have any desired shape: for example, cubic, rod like polyhedral, spherical or semi-spherical, rounded or semi-rounded, angular, irregular, et cetera. Shapes having a high aspect ratio, like needles, flakes, and fibers, are also contemplated for inclusion herein. The terms "particle" or "particulate" may also include an agglomeration comprising more than one individual particle, particulate, or the like. Additionally, a particle, particulate, or any desired agglomeration thereof may be composed of more than one type of material.

The term "polymer" includes, but is not limited to, homopolymers, copolymers, for example, block, graft, random, and alternating copolymers, terpolymers, etc., and blends and modifications thereof. Furthermore, unless otherwise specifically limited, the term "polymer" shall include all possible configurational isomers of the material. These configurations include, but are not limited to isotactic, syndiotactic, and atactic symmetries.

The term "polyolefin" as used herein generally includes, but is not limited to, materials such as polyethylene, polypropylene, polyisobutylene, polystyrene, ethylene vinyl acetate copolymer, and the like, the homopolymers, copolymers, terpolymers, etc., thereof, and blends and modifications thereof. The term "polyolefin" shall include all possible structures thereof, which include, but are not limited to, isotatic, synodiotactic, and random symmetries. Copolymers include atactic and block copolymers.

The term "polysiloxane" as used herein refers to polymerized siloxanes consisting of an inorganic silicon-oxygen backbone ( . . . —Si—O—Si—O—Si—O— . . . ) with organic side groups attached to the silicon atoms, which are four-coordinate. Furthermore, unless otherwise specifically limited, the term "polysiloxane" should include polymers comprising two of more siloxane repeating units.

The term "superabsorbent polymer" as used herein refers to water-swellable, water-insoluble organic or inorganic materials including superabsorbent polymers and superabsorbent polymer compositions capable, under the most favorable conditions, of absorbing at least about 10 times their weight, or at least about 15 times their weight, or at least about 25 times their weight in an aqueous solution containing 0.9 weight percent sodium chloride.

The term "superabsorbent polymer composition" as used herein refers to a superabsorbent polymer comprising a surface additive in accordance with the present invention.

The term "superabsorbent polymer preproduct" as used herein refers to a material that is produced by conducting all of the steps for making a superabsorbent polymer as described herein, up to and including drying the material, and coarse grinding in a crusher.

The term "surface crosslinking" as used herein refers to the level of functional crosslinks in the vicinity of the surface of the superabsorbent polymer particle, which is generally higher than the level of functional crosslinks in the interior of the superabsorbent polymer particle. As used herein, "surface" describes the outer-facing boundaries of the particle.

The term "thermoplastic" as used herein describes a material that softens when exposed to heat and which substantially returns to a non-softened condition when cooled to room temperature.

The term "% by weight" or "% wt" as used herein and referring to components of the superabsorbent polymer composition, is to be interpreted as based on the weight of the dry superabsorbent polymer composition, unless otherwise specified herein.

These terms may be defined with additional language in the remaining portions of the specification.

DETAILED DESCRIPTION

While typical aspects of embodiment and/or embodiments have been set forth for the purpose of illustration, this Detailed Description and the accompanying drawings should not be deemed to be a limitation on the scope of the invention. Accordingly, various modifications, adaptations, and alternatives may occur to one skilled in the art without departing from the spirit and scope of the present invention. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

The present invention is directed to a superabsorbent polymer having a Centrifuge Retention Capacity Increase. The capacity increase enables the superabsorbent polymer to have high gel strength and high absorption capacity at the same time. An idealized absorption capacity increase is illustrated in FIG. 1 showing an SAP having low absorption capacity initially and capacity increase over the swelling time.

An embodiment of the present invention includes a particulate superabsorbent polymer comprising a monomer and an internal crosslinking agent wherein the particulate superabsorbent polymer has a CRCI of 2 g/g or more, from 2 g/g to about 50 g/g, or from 2 g/g to about 40 g/g, or from about 3 g/g to about 30 g/g, as set forth herein in the CRCI Test. In another aspect, the CRCI may be dependent on the testing time.

CRC Increase Rate may be in the range from about 0.4 g/g/hour to about 10 g/g/hour, or from about 0.6 g/g/hour to about 8 g/g/hour. The testing time may be in the range of from about 2 hours to about 24 hours, or from about 2 hours to about 16 hours. The testing temperature may be in the range of from about 23° C. to about 50° C., preferably either about 23° C. (room temperature) or about 37° C. (body temperature). With the same testing time, the CRC at body temperature (CRC(bt)) is at least 2 g/g, or from 2 g/g to about 20 g/g higher than the CRC at body temperature (CRC(rt)).

The particulate superabsorbent polymer having CRCI of the present invention may be prepared by using a silane compound as the internal crosslinking agent. The silane compound comprises at least one carbon-carbon double bond and at least one Si—O bond.

Another embodiment of the present invention includes a superabsorbent polymer including an internal crosslinker agent which contains a silane compound comprising at least one vinyl group or allyl group directly attached to a silicon atom and at least one Si—O bond. The silane compound may be selected from one of the following:

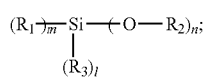
(I)

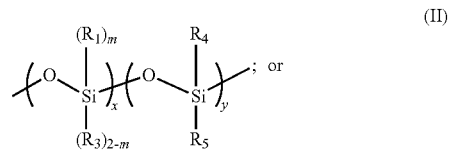

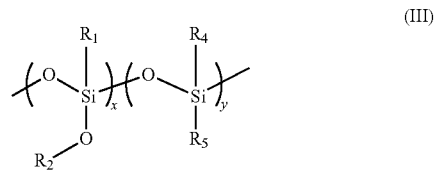

wherein
$R_1$ represents $C_2$ to $C_3$ alkenyl,
$R_2$ represents H, $C_1$ to $C_4$ alkyl, $C_2$ to $C_5$ alkenyl, $C_6$ to $C_8$ aryl, $C_2$ to $C_5$ carbonyl,
$R_3$ represents H, $C_1$ to $C_4$ alkyl, $C_6$ to $C_8$ aryl,
$R_4$ and $R_5$ independently represent H, $C_1$ to $C_4$ alkyl, $C_6$ to $C_8$ aryl,
m represents an integer of from 1 to 3, preferably 1 to 2,
n represents an integer of from 1 to 3, preferably 2 to 3,
l represents an integer of from 0 to 2, preferably 0 to 1,
m+n+l=4,
x represents an integer larger than 1, and
y represents an integer of 0 or larger than 0.

Illustrative of silanes, having at least one vinyl group or allyl group directly attached to a silicon atom and a Si—O bond, which may be utilized to provide the structure in formula (I) above include: vinylalkoxysilanes such as vinyltrimethoxysilane, methylvinyltrimethoxysilane, vinyltriethoxysilane, methylvinyltriethoxysilane, vinylmethyldimethoxysilane, vinylethyldiethoxysilane, and vinyltris(2-methoxyethoxy)silane; vinylacetoxysilanes, such as vinylmethyldiacetoxysilane, vinylethyldiacetoxysilane and vinyltriacetoxysilane; allylalkoxysilanes such as allyltrimethoxysilane, allylmethyldimethoxysilane, and allyltriethoxysilane; divinylalkoxysilanes and divinylacetoxysilanes such as divinyldimethoxysilane, divinyldiethoxysilane and divinyldiacetoxysilane; diallylalkoxysilanes and diallylacetoxysilanes such as diallyldimethoxysilane, diallyldiethoxysilane and diallyldiacetoxysilane; as well as other similar ethylenically unsaturated silane monomers containing one or more hydrolyzable groups. As will be appreciated by one skilled in the art given the present disclosure, use of compounds such as vinyltrichlorosilane in water or alcohol can provide structures in formula (I) above in which, for example, the group $R_1$ can be a vinyl group. It is also possible that more complex structures can be formed, for example, by reaction of vinyl silane with polyethylene glycol.

Illustrative of polysiloxanes, having at least one vinyl group or allyl group directly attached to a silicon atom, which may be utilized to provide the structure in formula (II) or (III) above include the polymers and copolymers of silanes having the structure in formula (I). Preferred examples include, but not limited to, polysiloxane comprising vinyl and methoxy groups (commercially available from Evonik Degussa Corporation, under the trade designation Dynasylan® 6490), polysiloxane comprising vinyl and ethoxy groups (commercially available from Evonik Degussa Corporation, under the trade designation Dynasylan® 6498), vinylmethylsiloxane homopolymers, vinylmethylsiloxane copolymers, vinyl terminated siloxane homopolymers, and vinyl terminated siloxane copolymers. However, it is contemplated that a wide range of polysiloxanes having vinyl functional groups provide the desired effects are effective crosslinking agents in accordance with the present invention.

In another embodiment, the superabsorbent polymer may include a second internal crosslinker which may comprise polyethylene glycol monoallyl ether acrylate, ethoxylated trimethylol propane triacrylate, and/or polyethylene glycol diacrylate.

Another embodiment of the present invention comprises a process of preparing a particulate superabsorbent polymer, having a CRCI from 2 g/g to about 50 g/g, by polymerizing at least one monomer, selected from an ethylenically unsaturated carboxylic acid, ethylenically unsaturated carboxylic acid and hydride, salts or derivatives thereof based on the superabsorbent polymer, and an internal crosslinking composition from about 0.001% by weight to about 5% by weight where the internal crosslinking composition includes a first and second internal crosslinking composition wherein one of the crosslinking compositions comprises a silane compound, having at least one vinyl group or one allyl group directly attached to a silicon atom, and at least one Si—O bond, into a hydrogel, preparing superabsorbent polymer particles from the superabsorbent polymer, and treating the superabsorbent polymer particles with surface additives including a surface crosslinking agent.

Another embodiment of the present invention is an absorbent article, such as diapers, training pants, incontinence products, other personal care or health care garments, including medical garments, or the like, comprising the superabsorbent polymer of the present invention.

A superabsorbent polymer as set forth in embodiments of the present invention is obtained by the initial polymerization of from about 55% to about 99.9% by weight of the superabsorbent polymer of polymerizable unsaturated acid group containing monomer. A suitable monomer includes any of those containing carboxyl groups, such as acrylic acid, methacrylic acid, or 2-acrylamido-2-methylpropanesulfonic acid, or mixtures thereof. It is desirable for at least about 50% by weight, and more desirable for at least about 75% by weight of the acid groups to be carboxyl groups.

The acid groups are neutralized to the extent of at least about 25 mol %, that is, the acid groups are desirably present as sodium, potassium, or ammonium salts. In some aspects, the degree of neutralization may be at least about 50 mol % or may be at least about 60 mol %. In some aspects, it is desirable to utilize polymers obtained by polymerization of acrylic acid or methacrylic acid, the carboxyl groups of which are neutralized to the extent of from about 50 mol % to about 80 mol %, in the presence of internal crosslinking agents.

In some aspects, the suitable monomer that can be copolymerized with the ethylenically unsaturated monomer may include, but is not limited to acrylamide, methacrylamide, hydroxyethyl acrylate, dimethylaminoalkyl(meth)-acrylate, ethoxylated (meth)-acrylates, dimethylaminopropylacrylamide, or acrylamidopropyltrimethylammonium chloride. Such monomer may be present in a range of from 0% to about 40% by weight of the copolymerized monomer.

The superabsorbent polymer includes crosslinking points wherein the superabsorbent polymer can be crosslinked with an internal crosslinking agent. Suitable internal crosslinker agents in this embodiment may include, but are not limited to a first internal crosslinker agent, which contains a silane compound comprising at least one vinyl group or one allyl group directly attached to a silicon atom, and at least one Si—O bond. Examples of internal silane crosslinkers suitable for the present invention are set forth with their chemical structure in Table 1.

TABLE 1

| Chemical | Chemical Structure |
|---|---|
| Vinyltriisopropenoxy silane | 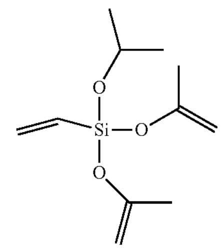 |
| Vinyltriacetoxysilane | 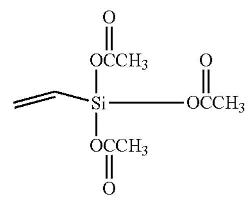 |
| Vinyltrimethoxysilane | 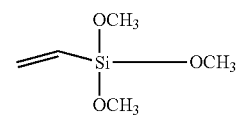 |
| Vinyltriethoxysilane | 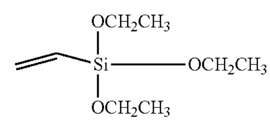 |
| Diethoxymethylvinyl silane | 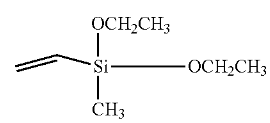 |
| Dynasylan ® 6490 (reaction vinyl siloxane oligomer, methoxy functional) | 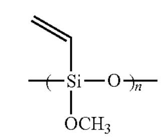 |
| Dynasylan ® 6498 (vinyl siloxane concentrate, oligomeric siloxane, ethoxy functional) | 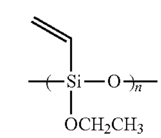 |
| Vinylmethyl polysiloxane | 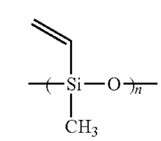 |

The superabsorbent polymer of the present invention may include an additional, or a second, internal crosslinking agent, which may be used in conjunction with the silane internal crosslinker. The additional, or second internal, crosslinker compositions generally includes at least two ethylenically unsaturated double bonds, or one ethylenically unsaturated double bond and one functional group that is reactive toward acid groups of the polymerizable unsaturated acid group containing monomer, or several functional groups that are reactive towards acid groups can be used as the internal crosslinking component and is desirably present during the polymerization of the polymerizable unsaturated acid group containing a monomer. The second internal crosslinker agents may include but are not limited to, aliphatic unsaturated amides, such as methylenebisacryl- or -methacrylamide or ethylenebisacrylamide; aliphatic esters of polyols or alkoxylated polyols with ethylenically unsaturated acids, such as di(meth)acrylates or tri(meth)acrylates of butanediol or ethylene glycol, polyglycols or trimethylolpropane; di- and triacrylate esters of trimethylolpropane which may be oxyalkylated, desirably ethoxylated, with about 1 to about 30 moles of alkylene oxide; acrylate and methacrylate esters of glycerol and pentaerythritol and of glycerol and pentaerythritol oxyethylated with desirably about 1 to about 30 mol of ethylene oxide; allyl compounds, such as allyl(meth)acrylate, alkoxylated allyl(meth)acrylate reacted with desirably about 1 to about 30 mol of ethylene oxide, triallyl cyanurate, triallyl isocyanurate, maleic acid diallyl ester, poly-allyl esters, tetraallyloxyethane, triallylamine, tetraallylethylenediamine, diols, polyols, hydroxy allyl or acrylate compounds and allyl esters of phosphoric acid or phosphorous acid; and monomers that are capable of crosslinking, such as N-methylol compounds of unsaturated amides, such as of methacrylamide or acrylamide, and the ethers derived therefrom. Ionic internal crosslinkers such as multivalent metal salts may also be employed. The additional, or second internal, crosslinker may be selected from polyethylene glycol monoallyl ether acrylate, ethoxylated trimethylol propane triacrylate, or polyethylene glycol diacrylate. Mixtures of the internal crosslinking agents mentioned can also be employed.

The content of the internal silane internal crosslinkers and second internal crosslinking agents is from about 0.001% to about 5% by weight, or from about 0.1% to about 3% by weight, based on the total amount of the polymerizable unsaturated acid group containing monomer. The superabsorbent polymer may include from about 9:1 to about 1:9, or about 7:1: to 1:7, of the internal crosslinker composition comprising silane and the second internal crosslinker.

In some aspects, initiators can be used for initiation of the free-radical polymerization. Suitable initiators include, but are not limited to, azo or peroxo compounds, redox systems or ultraviolet initiators, sensitizers, and/or radiation.

After polymerization, the superabsorbent polymer is generally formed into superabsorbent polymer particles, or particulate superabsorbent polymer. While superabsorbent polymer particles may be used by way of example of the physical form of superabsorbent polymer composition, the invention is not limited to this form and is applicable to other forms such as fibers, foams, films, beads, rods, and the like. The particulate superabsorbent polymer of the present invention generally includes particle sizes ranging from about 50 to about 1000 μm, or from about 150 to about 850 μm. The present invention may include at least about 40 wt % of the particles having a particle size from about 300 μm to about 600 μm, at least about 50 wt % of the particles having a particle size from about 300 μm to about 600 μm, or at least about 60 wt % of the particles having a particle size from about 300 μm to about 600 μm as measured by screening through a U.S. standard 30 mesh screen and retained on a U.S. standard 50 mesh screen. In addition, the size distribution of the superabsorbent polymer particles of the present invention may include less than about 30% by weight of particles having a size greater than about 600 microns, and less than about 30% by weight of particles having a size of less than about 300 microns as measured using for example a RO-TAP® Mechanical Sieve Shaker Model B available from W. S. Tyler, Inc., Mentor Ohio.

In one embodiment, the particulate superabsorbent polymer may then be surface treated with additional chemicals and treatments as set forth herein. In particular, the surface of the particulate superabsorbent polymer may be crosslinked, generally referred to as surface crosslinked, by the addition of a surface crosslinking agent and heat-treatment. In general, surface crosslinking is a process that is believed to increase the crosslink density of the polymer matrix in the vicinity of the particulate superabsorbent polymer surface with respect to the crosslinking density of the particle interior.

Desirable surface crosslinking agents may include chemicals with one or more functional groups that are reactive toward pendant groups of the polymer chains, typically the acid groups. Surface crosslinker agents may include compounds that comprise at least two functional groups which can react with functional groups of a polymer structure in a condensation reaction (condensation crosslinker), in an addition reaction or in a ring opening reaction. These compounds may include condensation crosslinkers such as, for example, diethylene glycol, triethylene glycol, polyethylene glycol, glycerine, polyglycerine, propylene glycol, diethanolamine, triethanolamine, polyoxypropylene, oxyethylene-oxypropylene block copolymers, sorbitan fatty acid esters, polyoxyethylene sorbitan fatty acid esters, trimethylolpropane, pentaerythritol, polyvinyl alcohol, sorbitol, 1,3-dioxolan-2-one (ethylene carbonate), 4-methyl-1,3-dioxolan-2-one (propylene carbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one as well as 1,3-dioxolan-2-one. The amount of the surface crosslinking agent may be present in an amount of from about 0.01% to about 5% by weight of the dry superabsorbent polymer composition, and such as from about 0.1% to about 3% by weight, and such as from about 0.1% to about 1% by weight, based on the weight of the dry particulate superabsorbent polymer composition.

After the particulate superabsorbent polymer have been brought into contact with the surface crosslinker or with the fluid comprising the surface crosslinker, the treated particulate superabsorbent polymer are heat treated which may include heating the coated particulate superabsorbent polymer to a temperature of from about 50 to about 300° C., or from about 75 to about 275° C., or from about 150 to about 250° C., so that the outer region of the polymer structures is more strongly crosslinked compared to the inner region (i.e., surface crosslinking). The duration of the heat treatment is limited by the risk that the desired property profile of the polymer structures will be destroyed as a result of the effect of heat In one particular aspect of surface crosslinking, the particulate superabsorbent polymer is coated or surface-treated with an alkylene carbonate followed by heating to affect surface crosslinking, which can improve the surface crosslinking density and the gel strength characteristics of the superabsorbent polymer particle. More specifically, the surface crosslinking agent is coated onto the superabsorbent polymer particulate by mixing the particulate superabsorbent polymer with an aqueous alcoholic solution of the alkylene carbonate surface crosslinking agent. The amount of alcohol in the aqueous alcoholic solution may be determined by the solubility of the alkylene carbonate and is kept as low as possible for various reasons, for instance, for protection against explosions. Suitable alcohols are methanol, isopropanol, ethanol, butanol, or butyl glycol, as well as mixtures of these alcohols. In some aspects, the solvent desirably is water, which typically is used in an amount of about 0.3% by weight to about 5.0% by weight, based on the weight of the dry superabsorbent polymer.

In other aspects, the alkylene carbonate surface crosslinking agent is dissolved in water without any alcohol. In still other aspects, the alkylene carbonate surface crosslinking agent may be applied from a powder mixture, for example, with an inorganic carrier material, such as silicone dioxide ($SiO_2$), or in a vapor state by sublimation of the alkylene carbonate.

To achieve the desired surface crosslinking properties, the alkylene carbonate should be distributed evenly on the particulate superabsorbent polymer. For this purpose, mixing is effected in suitable mixers known in the art, such as fluidized bed mixers, paddle mixers, rotary drum mixers, or twin-worm mixers. It is also possible to carry out the coating of the particulate superabsorbent polymer during one of the process steps in the production of the particulate superabsorbent polymer. In one particular aspect, a suitable process for this purpose is the inverse suspension polymerization process.

The heat treatment, which follows the coating treatment of the particulate superabsorbent polymer, may be carried out as follows. In general, the heat treatment is at a temperature of from about 100° C. to about 300° C. Lower temperatures are possible if highly reactive epoxide crosslinking agents are used. However, if alkylene carbonates are used, then the thermal treatment is suitably at a temperature of from about 150° C. to about 250° C. In this particular aspect, the treatment temperature depends on the dwell time and the kind of alkylene carbonate. For example, at a temperature of about 150° C., the thermal treatment is carried out for one hour or longer. In contrast, at a temperature of about 250° C., a few minutes (e.g., from about 0.5 minutes to about 5 minutes) are sufficient to achieve the desired surface crosslinking properties. The thermal treatment may be carried out in conventional dryers or ovens known in the art.

In addition to surface crosslinking, the particulate superabsorbent polymer compositions may be further surface treated with other chemical compositions. In some aspects, the particulate superabsorbent polymer composition of the present invention may be surface treated with from 0% to about 5% by weight, and from about 0.001% to about 5% by weight, or from about 0.01% to about 0.5% by weight of the dry superabsorbent polymer composition of a polymeric coating, such as a thermoplastic coating, or a cationic coating, or a combination of a thermoplastic coating and a cationic coating. In some particular aspects, the polymeric coating desirably is a polymer that may be in a solid, emulsion, suspension, colloidal, or solubilized state, or combinations thereof. Polymeric coatings suitable for this invention may include, but are not limited to, a thermoplastic coating having a thermoplastic melt temperature wherein the polymeric coating is applied to the particle surface coincident with or followed by a temperature of the treated superabsorbent polymer particle at about the thermoplastic melt temperature.

Examples of thermoplastic polymers include polyolefin, polyethylene, polyester, polyamide, polyurethane, styrene polybutadiene, linear low density polyethylene (LLDPE), ethylene acrylic acid copolymer (EAA), ethylene alkyl methacrylate copolymer (EMA), polypropylene (PP), maleated polypropylene, ethylene vinyl acetate copolymer (EVA), polyester, polyamide, and blends of all families of polyolefins, such as blends of PP, EVA, EMA, EEA, EBA, HDPE, MDPE, LDPE, LLDPE, and/or VLDPE, may also be advantageously employed. The term polyolefin as used herein is defined above. In particular aspects, maleated polypropylene is a preferred thermoplastic polymer for use in the present invention. A thermoplastic polymer may be functionalized to have additional benefits such as water solubility or dispersability.

Polymeric coatings of this invention may also include a cationic polymer. A cationic polymer as used herein refers to a polymer or mixture of polymers comprising a functional group or groups having a potential of becoming positively charged ions upon ionization in an aqueous solution. Suitable functional groups for a cationic polymer include, but are not limited to, primary, secondary, or tertiary amino groups, imino groups, imido groups, amido groups, and quaternary ammonium groups. Examples of synthetic cationic polymers include the salts or partial salts of poly(vinyl amines), poly (allylamines), poly(ethylene imine), poly(amino propanol vinyl ethers), poly(acrylamidopropyl trimethyl ammonium chloride), poly(diallyldimethyl ammonium chloride). Examples of natural-based cationic polymers include partially deacetylated chitin, chitosan, and chitosan salts. Synthetic polypeptides such as polyasparagins, polylysines, polyglutamines, and polyarginines are also suitable cationic polymers.

The particulate superabsorbent polymer compositions according to the invention may be surface treated with from about 0.01% to about 2% by weight, or from about 0.01% to about 1% by weight based on the dry superabsorbent polymer composition of a water-insoluble inorganic metal compound. The water-insoluble inorganic metal compound may include a cation selected from aluminum, titanium, calcium, or iron and an anion selected from phosphate, borate, or chromate. An example of a water insoluble inorganic metal compound includes aluminum phosphate. The inorganic metal compound may have a mass median particle size of less than about 2 μm, and may have a mass median particle size of less than about 1 μm.

The inorganic metal compound can be applied in the dry physical form to the surface of the particulate superabsorbent polymer composition. For this, the particulate superabsorbent polymer composition may be intimately mixed with the finely divided inorganic metal compound. The finely divided inorganic metal compound is usually added at room temperature to the superabsorbent polymer particles and mixed in until a homogeneous mixture is present. For this purpose, mixing is effected in suitable mixers known in the art, such as fluidized bed mixers, paddle mixers, rotary drum mixers, or twin-worm mixers. The mixing of the particulate superabsorbent polymer compositions with the finely divided water insoluble inorganic metal compound may take place before or after any surface crosslinking, for example during the application of the surface crosslinking agent.

Alternatively, a suspension of a finely divided water insoluble inorganic metal compounds can be prepared and applied to a particulate water absorbent polymer. The suspension is applied, for example, by spraying. Useful dispersion media for preparing the suspension include water, organic solvents such as alcohols, for example methanol, ethanol, isopropanol, ketones, for example acetone, methyl ethyl ketone, or mixtures of water with the aforementioned organic solvents. Other useful dispersion media include dispersion aids, surfactants, protective colloidals, viscosity modifiers, and other auxiliaries to assist in the preparation of the suspension. The suspension can be applied in conventional reaction mixers or mixing and drying systems as described above at a temperature in the range from room temperature to less than the boiling point of the dispersion medium, preferably at about room temperature. It is appropriate to combine the application of the suspension with a surface crosslinking step by dispersing the finely divided water insoluble metal salt in the solution of the surface crosslinking agent. Alternatively, the suspension can also be applied before or after the surface crosslinking step. The application of the slurry may be followed by a drying step.

In some aspects, the particulate superabsorbent polymer compositions according to the invention may include from 0% to about 5%, or in the alternative from about 0.01% to about 3%, by weight of the dry superabsorbent polymer composition of silica. Examples of silica include fumed silica, precipitated silica, silicon dioxide, silicic acid, and silicates. In some particular aspects, microscopic noncrystalline silicon dioxide is desirable. In some aspects, the particle diameter of the inorganic powder can be 1,000 μm or smaller, such as 100 μm or smaller.

In some aspects, the particulate superabsorbent polymer compositions may also include from 0% to about 30% by weight of the dry superabsorbent polymer composition, such as from about 0.1% to about 5% by weight, of water-soluble polymers based by weight of the dry superabsorbent polymer composition, such as partly or completely hydrolyzed polyvinyl acetate, polyvinylpyrrolidone, starch or starch derivatives, polyglycols, polyethylene oxides, polypropylene oxides, or polyacrylic acids. In some particular aspects, the water-soluble polymers are desirably in polymerized-in form.

In some aspects, additional surface additives may optionally be employed with the particulate superabsorbent polymer compositions, including odor-binding substances, such as cyclodextrins, zeolites, inorganic or organic salts, and similar materials; anti-caking additives, flow modification agents, surfactants, viscosity modifiers, and the like. In addition, surface additives may be employed that perform several roles during surface modifications. For example, a single additive may be a surfactant, viscosity modifier, and may react to crosslink polymer chains.

In some aspects, the particulate superabsorbent polymer compositions of the present invention may be, after a heat treatment step, treated with water so that the superabsorbent polymer composition has a water content of up to about 10% by weight of the superabsorbent polymer composition. This water may be added, with one or more of the surface additives from above, to the superabsorbent polymer.

The superabsorbent polymer according to the invention may be desirably prepared by two methods. The composition can be prepared continuously or discontinuously in a large-scale industrial manner, the after-crosslinking according to the invention being carried out accordingly.

According to one method, the partially neutralized monomer, such as acrylic acid, is converted into a gel by free-radical polymerization in aqueous solution in the presence of crosslinking agents and any further components, and the gel is comminuted, dried, ground, and sieved off to the desired particle size. This polymerization can be carried out continuously or discontinuously. For the present invention, the size of the high-capacity superabsorbent polymer composition particles is dependent on manufacturing processes including milling and sieving. It is well known to those skilled in the art that particle size distribution of the superabsorbent polymer particles resembles a normal distribution or a bell shaped curve. It is also known that for various reasons, the normal distribution of the particle size distribution may be skewed in either direction.

According to another method, inverse suspension and emulsion polymerization can also be used for preparation of the products according to the invention. According to these processes, an aqueous, partly neutralized solution of monomer, such as acrylic acid, is dispersed in a hydrophobic, organic solvent with the aid of protective colloids and/or emulsifiers, and the polymerization is started by free radical initiators. The internal crosslinking agents may be either dissolved in the monomer solution and are metered in together with this, or are added separately and optionally during the polymerization. The addition of a water-soluble polymer as the graft base optionally takes place via the monomer solution or by direct introduction into the oily phase. The water is then removed azeotropically from the mixture, and the polymer is filtered off and optionally dried. Internal crosslinking can be carried out by polymerizing-in a polyfunctional crosslinking agent dissolved in the monomer solution and/or by reaction of suitable crosslinking agents with functional groups of the polymer during the polymerization steps.

The result of these methods is a superabsorbent polymer or a superabsorbent polymer preproduct. A superabsorbent polymer preproduct as used herein is produced by repeating all of the steps for making the superabsorbent, up to and including drying the material, and coarse grinding in a crusher, and removing particles greater than about 850 microns and smaller than about 150 microns.

The particulate superabsorbent polymer composition of the present invention exhibits certain characteristics, or properties, as measured by Centrifuge Retention Capacity, Centrifuge Retention Capacity Increase, Centrifuge Retention Capacity Increase Rate (CRCIR), Absorbency Under Load at about 0.9 psi (AUL(0.9 psi)), and Gel Bed Permeability (GBP). The Vortex Time measures the speed of the polymer in absorbing saline solution and is expressed in seconds.

The resultant CRC is stated as grams of liquid retained per gram weight of the sample (g/g) and may be from about 20 g/g to 60 g/g, from about 25 g/g to about 55 g/g, or from about 27 g/g to about 50 g/g.

The CRCI is stated as grams of liquid retained per gram weight of the sample (g/g) and may be from 2 g/g to 50 g/g or from about 3 g/g to about 40 g/g.

The Centrifuge Retention Capacity Increase Rate (CRCIR) Test measures the rate of Centrifuge Retention Capacity Increase per hour difference between the CRC(initial) Test and the CRC(second) Test and is measured in terms of g/g/hr. The CRC Increase Rate may be from about 0.4 to about 10 g/g/hr, or from about 0.5 to about 5 g/g/hr.

The Absorbency Under Load at about 0.9 psi (AUL(0.9 psi)) may range from about 12 g/g to about 30 g/g, or from about 15 g/g to about 25 g/g.

Permeability is a measure of the effective connectedness of a porous structure, be it a mat of fiber, or a slab of foam or, in this case, crosslinked polymers, and may be specified in terms of the void fraction, and extent of connectedness of the particulate superabsorbent polymer composition. Gel permeability is a property of the mass of particles as a whole and is related to particle size distribution, particle shape, and the connectedness of the open pores between the particles, shear modulus, and surface modification of the swollen gel. In practical terms, the gel permeability of the superabsorbent polymer composition is a measure of how rapidly liquid flows through the mass of swollen particles. Low gel permeability indicates that liquid cannot flow readily through the superabsorbent polymer composition, which is generally referred to as gel blocking, and that any forced flow of liquid (such as a second application of urine during use of the diaper) must take an alternate path (e.g., diaper leakage). Gel Bed Permeability (GBP) may range from about $10 \times 10^{-8}$ cm$^2$ to about $300 \times 10^{-8}$ cm$^2$, or from $10 \times 10^{-8}$ cm$^2$ to about $200 \times 10^{-8}$ cm$^2$.

The Vortex time for the particulate superabsorbent polymer and the particulate superabsorbent polymer composition may be from about 20 to about 180 sec, or from about 60 to about 130 sec, or from about 70 to about 125 sec.

As shown in FIG. 1, it is a goal of the present invention to increase the absorption capacity over time, wherein such superabsorbent polymers may offer the advantage of high gel strength in the short term and high absorption capacity in the long term.

Figure 2:
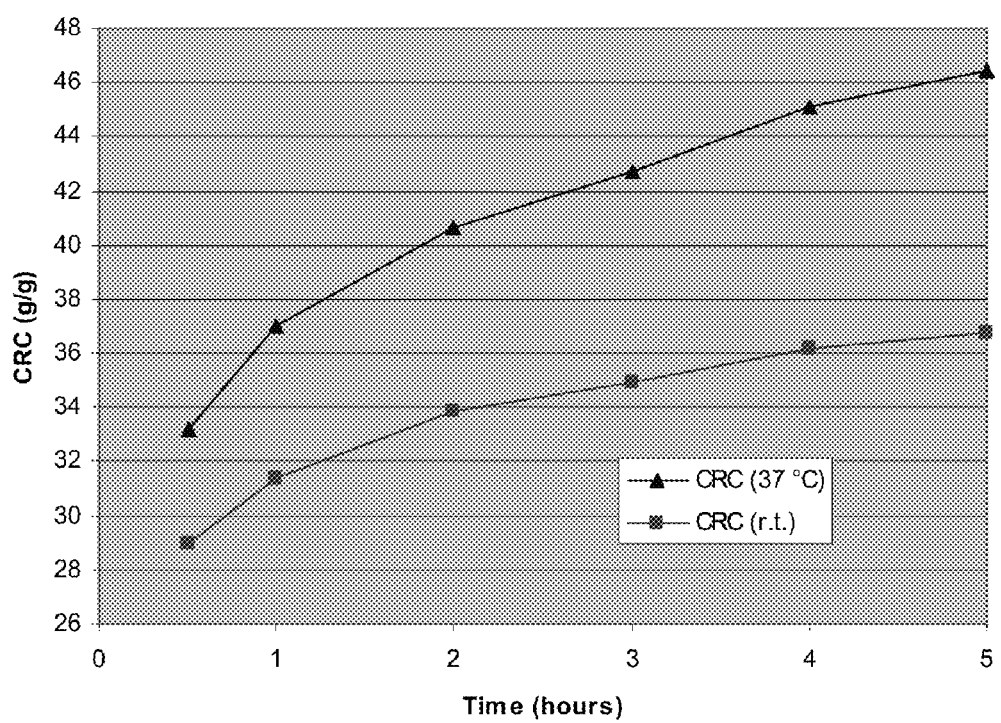
FIG. 2 contains plots of CRC vs. swelling time for particulate SAP preproduct from present invention.

FIG. 2 displays CRC(rt) and CRC(bt) of a SAP preproduct comprising 0.5% of Dynasylan® 6490. It shows that CRC increases over the time either at room temperature or body temperature. In addition, it shows that CRC at body temperature is higher than CRC at room temperature at any specific time. Furthermore, it shows that CRC increases faster at body temperature than at room temperature.

Figure 3:
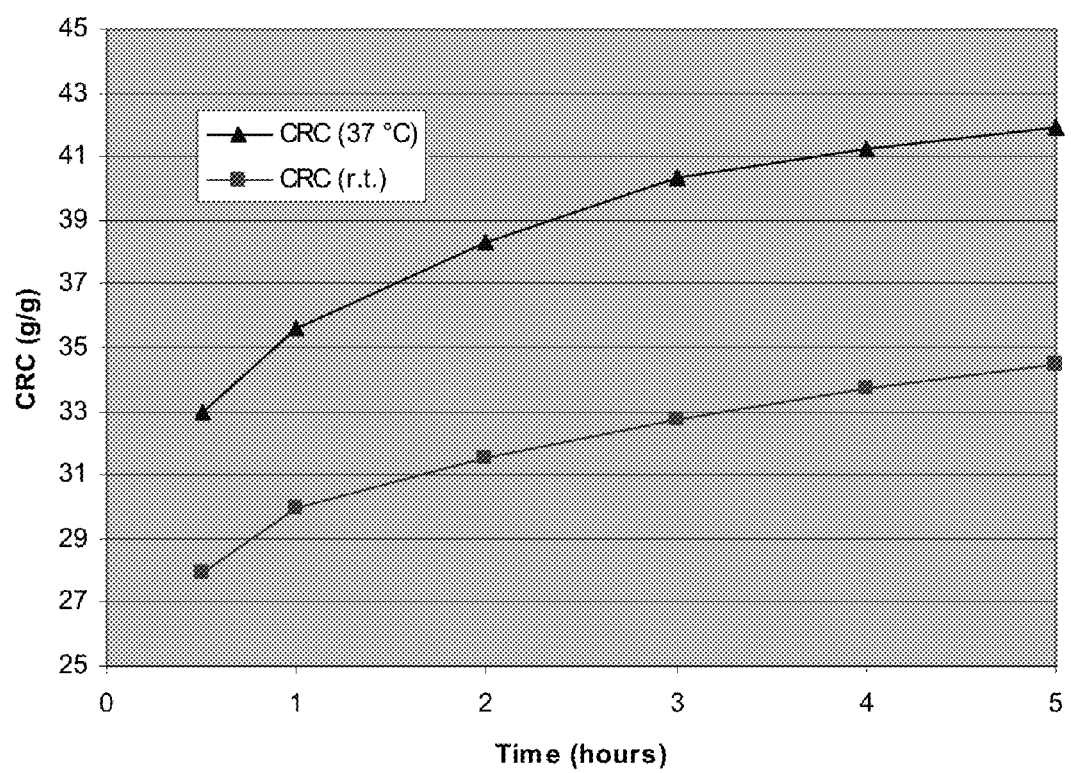
FIG. 3 contains plots of CRC vs. swelling time for particulate SAP composition from present invention.

FIG. 3 displays CRC(rt) and CRC(bt) of a surface crosslinked SAP comprising 0.5% of Dynasylan® 6490 as internal crosslinker. It shows that CRC increases over the time either at room temperature or body temperature. In addition, it demonstrates that CRC at body temperature is higher than CRC at room temperature at any specific time. Furthermore, it shows that CRC increases faster at body temperature than at room temperature.

Figure 4:
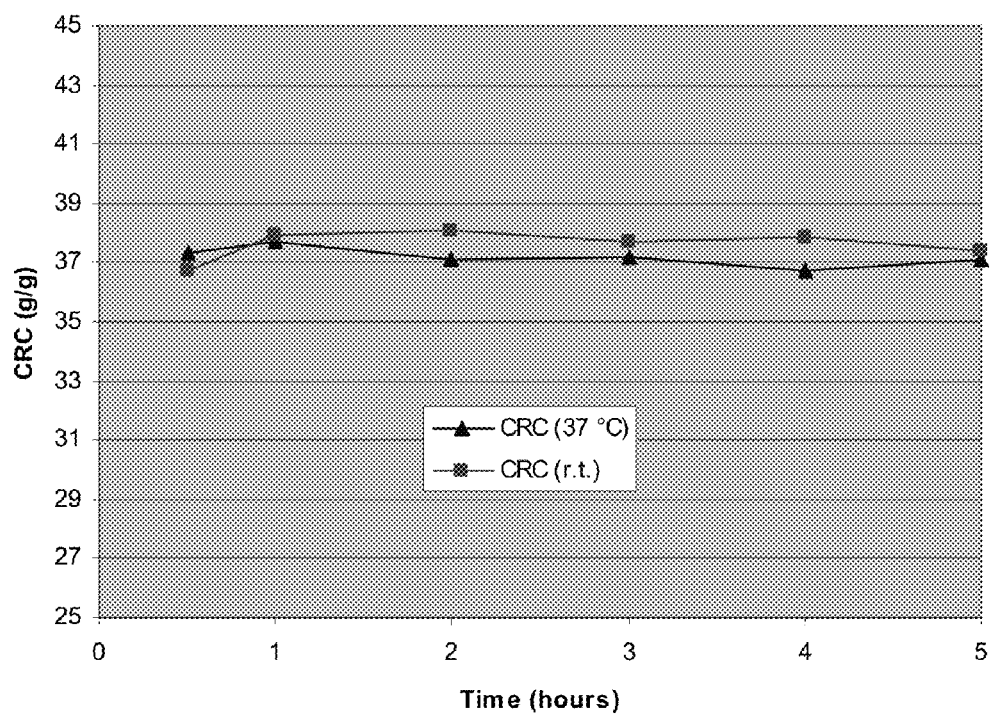
FIG. 4 contains plots of CRC vs. swelling time for prior art particulate SAP composition.

FIG. 4, Prior Art, displays CRC(rt) and CRC(bt) of a surface crosslinked SAP comprising only conventional internal crosslinker. It shows that CRC was essentially constant over time or at different temperatures.

The superabsorbent polymer compositions according to the present invention can be employed in many absorbent articles including sanitary towels, diapers, or wound coverings, and they have the property that they rapidly absorb large amounts of menstrual blood, urine, or other body fluids. Since the agents according to the invention retain the absorbed liquids even under pressure and are also capable of distributing further liquid within the construction in the swollen state, they are more desirably employed in higher concentrations, with respect to the hydrophilic fiber material, such as fluff, when compared to conventional current superabsorbent compositions. They are also suitable for use as a homogeneous superabsorber layer without fluff content within the diaper construction, as a result of which particularly thin articles are possible. The polymers are furthermore suitable for use in hygiene articles (incontinence products) for adults.

Absorbent articles, like diapers, may include (a) a liquid pervious topsheet; (b) a liquid impervious backsheet; (c) a core positioned between (a) and (b) and comprising about 10% to 100%, and preferably about 50% to about 100%, by weight of the present polyamine-coated SAP particles, and 0% to 90% by weight of hydrophilic fiber material; (d) optionally a tissue layer positioned directly above and below said core (c); and (e) optionally an acquisition layer positioned between (a) and (c).

Test Procedures

Water Content

Centrifuge Retention Capacity Test (CRC).

The CRC Test measures the ability of the superabsorbent polymer to retain liquid therein after being saturated and subjected to centrifugation under controlled conditions. The resultant retention capacity is stated as grams of liquid retained per gram weight of the sample, (g/g). The sample to be tested is prepared from particles that are pre-screened through a U.S. standard 30-mesh screen and retained on a U.S. standard 50-mesh screen. As a result, the superabsorbent polymer sample comprises particles sized in the range of about 300 to about 600 microns. The particles can be pre-screened by hand or automatically.

The retention capacity is measured by placing about 0.2 grams of the pre-screened superabsorbent polymer sample into a water-permeable bag that will contain the sample while allowing a test solution (0.9 weight percent sodium chloride in distilled water) to be freely absorbed by the sample. A heat-sealable tea bag material, such as that available from Dexter Corporation (having a place of business in Windsor Locks, Conn., U.S.A.) as model designation 1234T heat sealable filter paper works well for most applications. The bag is formed by folding a 5-inch by 3-inch sample of the bag material in half and heat-sealing two of the open edges to form a 2.5-inch by 3-inch rectangular pouch. The heat seals are about 0.25 inches inside the edge of the material. After the sample is placed in the pouch, the remaining open edge of the pouch is also heat-sealed. Empty bags are also made to serve as controls. Three samples are prepared for each superabsorbent polymer composition to be tested.

The sealed bags are submerged in a pan containing the test solution at an assigned testing temperature, making sure that the bags are held down until they are completely wetted. After wetting, the samples remain in the solution for an assigned period of testing time, at which time they are removed from the solution and temporarily laid on a non-absorbent flat surface.

The wet bags are then placed into the basket wherein the wet bags are separated from each other and are placed at the outer circumferential edge of the basket, wherein the basket is of a suitable centrifuge capable of subjecting the samples to a g-force of about 350. One suitable centrifuge is a CLAY ADAMS DYNAC II, model #0103, having a water collection basket, a digital rpm gauge, and a machined drainage basket adapted to hold and drain the flat bag samples. Where multiple samples are centrifuged, the samples are placed in opposing positions within the centrifuge to balance the basket when spinning The bags (including the wet, empty bags) are centrifuged at about 1,600 rpm (e.g., to achieve a target g-force of about 350 g force with a variance from about 240 to about 360 g force), for 3 minutes. G force is defined as an unit of inertial force on a body that is subjected to rapid acceleration or gravity, equal to 32 ft/sec$^2$ at sea level. The bags are removed and weighed, with the empty bags (controls) being weighed first, followed by the bags containing the superabsorbent polymer composition samples. The amount of solution retained by the superabsorbent polymer sample, taking into account the solution retained by the bag itself, is the centrifuge retention capacity (CRC) of the superabsorbent polymer, expressed as grams of fluid per gram of superabsorbent polymer. More particularly, the retention capacity is determined by the following equation:

$$CRC = [\text{sample/bag after centrifuge} - \text{empty bag after centrifuge} - \text{dry sample weight}] / \text{dry sample weight}$$

The three samples are tested, and the results are averaged to determine the CRC of the superabsorbent polymer composition.

CRC(rt, 0.5 hr) is measured with a testing temperature of about 23° C. (room temperature) and a testing time of 0.5 hour.

CRC(rt, 5 hr) is measured with a testing temperature of about 23° C. (room temperature) and a testing time of 5 hours.

CRC(rt, 16 hr) is measured with a testing temperature of about 23° C. (room temperature) and a testing time of 16 hours.

CRC(bt, 0.5 hr) is measured with a testing temperature of about 37° C. (body temperature) and a testing time of 0.5 hour.

CRC(bt, 5 hr) is measured with a testing temperature of about 37° C. (body temperature) and a testing time of 5 hours.

Centrifuge Retention Capacity Increase (CRCI) Test

The Centrifuge Retention Capacity Increase (CRCI) Test measures the increase in the CRC that occurs and is calculated as the difference between the second CRC Test and the first CRC(rt,0.5 hr) Test and is determined by the following equation:

CRC Increase=second CRC−(CRC(rt,0.5 hr).

For example, CRCI's in the present invention are determined by the following equations:

At room temperature, CRCI(rt)=CRC(rt, 5 hr).−CRC(rt, 0.5 hr).

At body temperature, CRCI(bt)=CRC(bt, 5 hr).−CRC(bt, 0.5 hr).

CRCI(rt) and CRCI(bt) are collectively referred to as CRCI.

Centrifuge Retention Capacity Increase Rate Test (CRCIR)

The CRCIR measures the ability of the particulate superabsorbent polymer to gain additional CRC over the time when contacted with a liquid. It is tested by measuring the CRC and at an assigned testing temperature for two different testing times. The second testing time is at least one hour longer than the first testing time. The resultant CRCIR is stated as grams of additional liquid retained per gram weight of the sample per hour (g/g/hour).

For example, CRCIR in the present invention are determined by the following equations:

At room temperature: CRCIR(rt)=[CRC(rt, 5 hr)−(CRC(rt, 0.5 hr)]/4.5

At body temperature: CRCIR(bt)=[CRC(bt, 5 hr)−(CRC(bt, 0.5 hr)]/4.5

CRCIR(rt) and CRCIR(bt) are collectively referred to as CRCIR.

Free-Swell Gel Bed Permeability Test (FSGBP)

Figure 5:
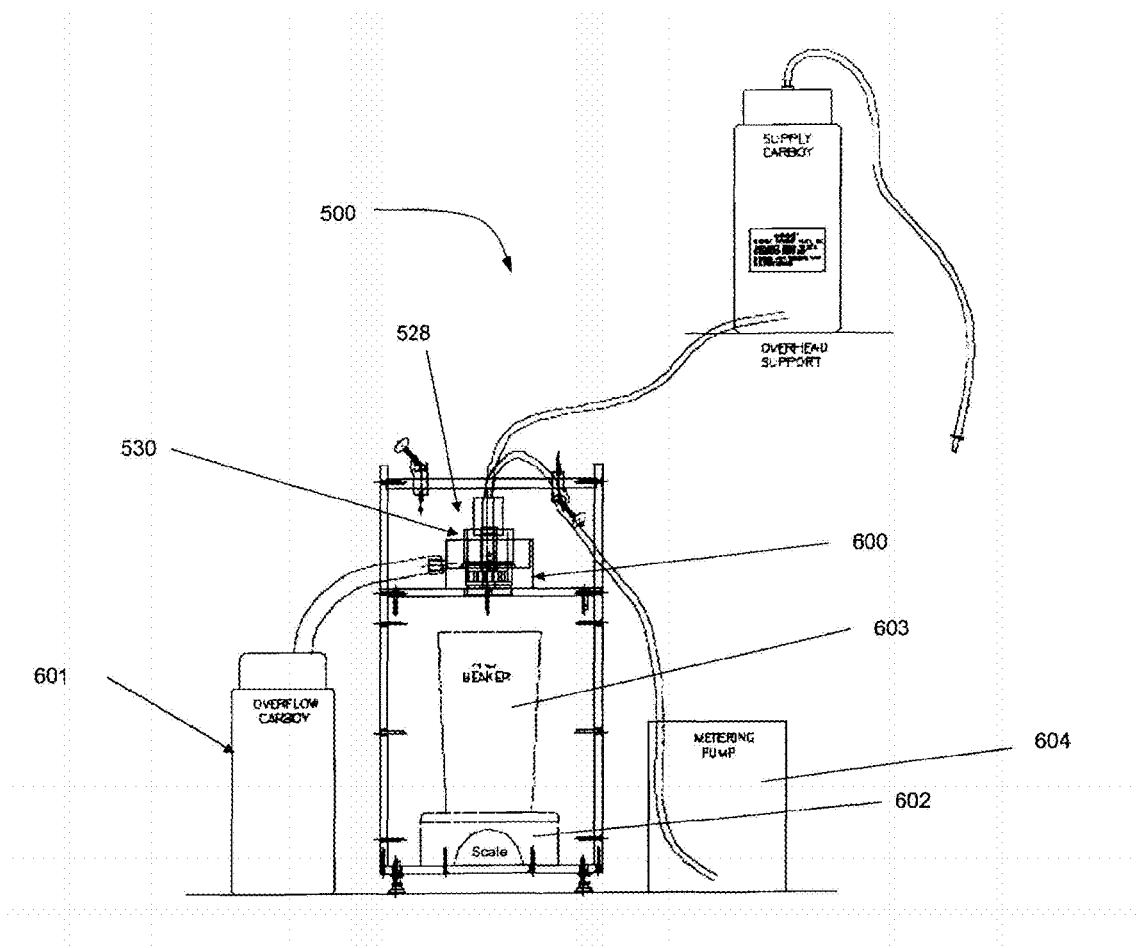
FIG. 5 is a side view of the test apparatus employed for the Free Swell Gel Bed Permeability Test.
Figure 6:
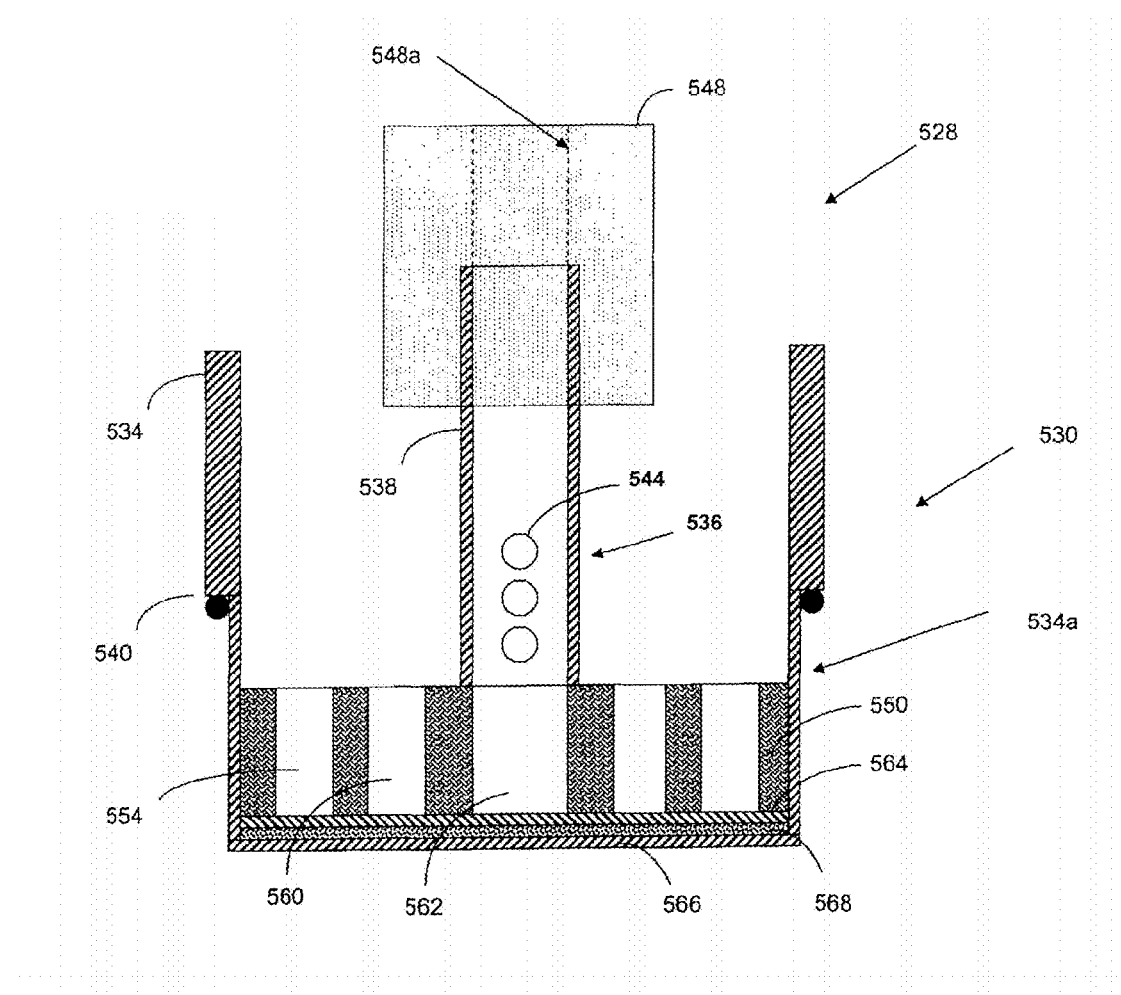
FIG. 6 is a cross-sectional side view of a cylinder/cup assembly employed in the Free Swell Gel Bed Permeability Test apparatus shown in FIG. 5.
Figure 7:
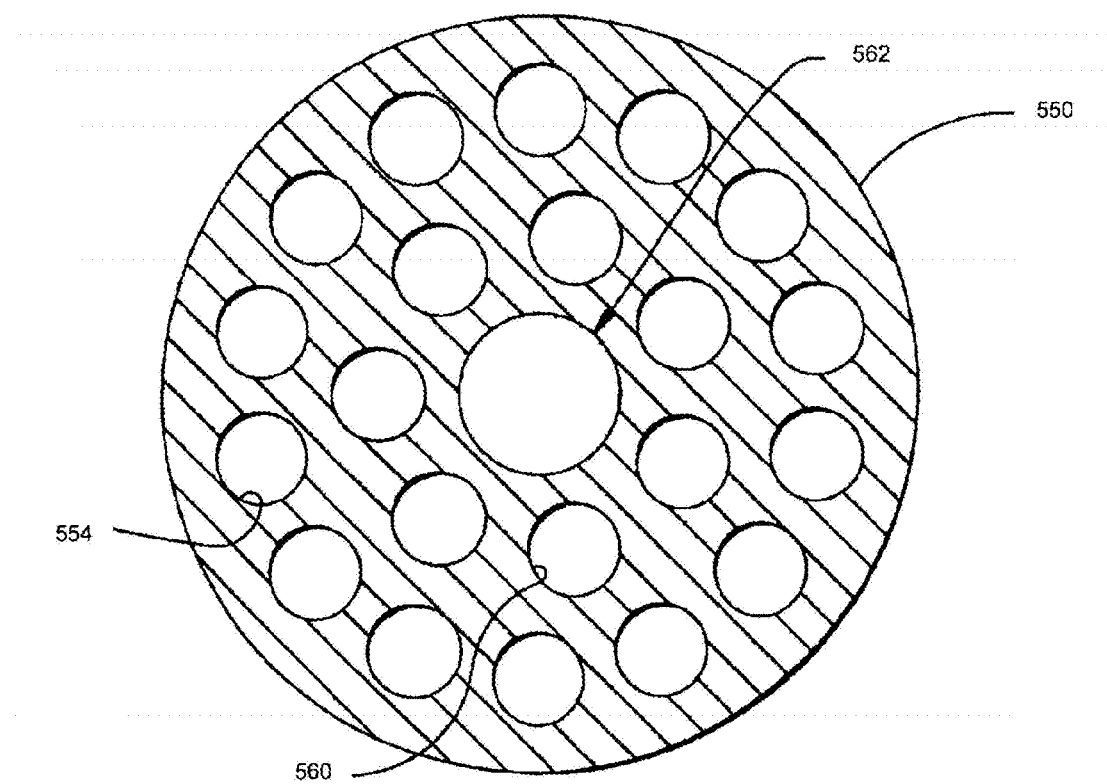
FIG. 7 is a top view of a plunger employed in the Free Swell Gel Bed Permeability Test apparatus shown in FIG. 5.

As used herein, the Free-Swell Gel Bed Permeability Test, also referred to as the Gel Bed Permeability (GBP) Under 0 psi Swell Pressure Test, determines the permeability of a swollen bed of gel particles (e.g., such as the surface treated absorbent material or the superabsorbent material prior to being surface treated), under what is commonly referred to as "free swell" conditions. The term "free swell" means that the gel particles are allowed to swell without a restraining load upon absorbing test solution as will be described. A suitable apparatus for conducting the Gel Bed Permeability Test is shown in FIGS. 5, 6, and 7 and indicated generally as 500. The test apparatus assembly 528 comprises a sample container, generally indicated at 530, and a plunger, generally indicated at 536. The plunger comprises a shaft 538 having a cylinder hole bored down the longitudinal axis and a head 550 positioned at the bottom of the shaft. The shaft hole 562 has a diameter of about 16 mm. The plunger head is attached to the shaft, such as by adhesion. Twelve holes 544 are bored into the radial axis of the shaft, three positioned at every 90 degrees having diameters of about 6.4 mm. The shaft 538 is machined from a LEXAN rod or equivalent material and has an outer diameter of about 2.2 cm and an inner diameter of about 16 mm.

The plunger head 550 has a concentric inner ring of seven holes 560 and an outer ring of 14 holes 554, all holes having a diameter of about 8.8 millimeters as well as a hole of about 16 mm aligned with the shaft. The plunger head 550 is machined from a LEXAN rod or equivalent material and has a height of approximately 16 mm and a diameter sized such that it fits within the cylinder 534 with minimum wall clearance but still slides freely. The total length of the plunger head 550 and shaft 538 is about 8.25 cm, but can be machined at the top of the shaft to obtain the desired mass of the plunger 536.

The plunger 536 comprises a 100 mesh stainless steel cloth screen 564 that is biaxially stretched to tautness and attached to the lower end of the plunger 536. The screen is attached to the plunger head 550 using an appropriate solvent that causes the screen to be securely adhered to the plunger head 550. Care must be taken to avoid excess solvent migrating into the open portions of the screen and reducing the open area for liquid flow. Acrylic solvent Weld-on 4 from IPS Corporation (having a place of business in Gardena, Calif., USA) is a suitable solvent.

The sample container 530 comprises a cylinder 534 and a 400 mesh stainless steel cloth screen 566 that is biaxially stretched to tautness and attached to the lower end of the cylinder 534. The screen is attached to the cylinder using an appropriate solvent that causes the screen to be securely adhered to the cylinder. Care must be taken to avoid excess solvent migrating into the open portions of the screen and reducing the open area for liquid flow. Acrylic solvent Weld-on 4 from IPS Corporation (having a place of business in Gardena, Calif., USA) is a suitable solvent. A gel particle sample, indicated as 568 in FIG. 2, is supported on the screen 566 within the cylinder 534 during testing.

The cylinder 534 may be bored from a transparent LEXAN rod or equivalent material, or it may be cut from a LEXAN tubing or equivalent material, and has an inner diameter of about 6 cm (e.g., a cross-sectional area of about 28.27 $cm^2$), a wall thickness of about 0.5 cm and a height of approximately 7.95 cm. A step is machined into the outer diameter of the cylinder 534 such that a region 534a with an outer diameter of 66 mm exists for the bottom 31 mm of the cylinder 534. An o-ring 540 which fits the diameter of region 534a may be placed at the top of the step.

The annular weight 548 has a counter-bored hole about 2.2 cm in diameter and 1.3 cm deep so that it slips freely onto the shaft 538. The annular weight also has a thru-bore 548a of about 16 mm. The annular weight 548 can be made from stainless steel or from other suitable materials resistant to corrosion in the presence of the test solution, which is 0.9 weight percent sodium chloride solution in distilled water. The combined weight of the plunger 536 and annular weight 548 equals approximately 596 grams (g), which corresponds to a pressure applied to the sample 568 of about 0.3 pounds per square inch (psi), or about 20.7 $dynes/cm^2$ (2.07 kPa), over a sample area of about 28.27 $cm^2$.

When the test solution flows through the test apparatus during testing as described below, the sample container 530 generally rests on a weir 600. The purpose of the weir is to divert liquid that overflows the top of the sample container 530 and diverts the overflow liquid to a separate collection device 601. The weir can be positioned above a scale 602 with a beaker 603 resting on it to collect saline solution passing through the swollen sample 568.

To conduct the Gel Bed Permeability Test under "free swell" conditions, the plunger 536, with the weight 548 seated thereon, is placed in an empty sample container 530 and the height from the top of the weight 548 to the bottom of the sample container 530 is measured using a suitable gauge accurate to 0.01 mm. The force the thickness gauge applies during measurement should be as low as possible, preferably less than about 0.74 Newtons. It is important to measure the height of each empty sample container 530, plunger 536, and weight 548 combination and to keep track of which plunger 536 and weight 548 is used when using multiple test apparatus. The same plunger 536 and weight 548 should be used for measurement when the sample 568 is later swollen following saturation. It is also desirable that the base that the sample cup 530 is resting on is level, and the top surface of the weight 548 is parallel to the bottom surface of the sample cup 530.

The sample to be tested is prepared from superabsorbent polymer composition particles which are prescreened through a U.S. standard 30 mesh screen and retained on a U.S. standard 50 mesh screen. As a result, the test sample comprises particles sized in the range of about 300 to about 600 microns. The superabsorbent polymer particles can be prescreened with, for example, a RO-TAP Mechanical Sieve Shaker Model B available from W. S. Tyler, Inc., Mentor Ohio. Sieving is conducted for 10 minutes. Approximately 2.0 grams of the sample is placed in the sample container 530 and spread out evenly on the bottom of the sample container. The container, with 2.0 grams of sample in it, without the plunger 536 and weight 548 therein, is then submerged in the 0.9% saline solution for a time period of about 60 minutes to saturate the sample and allow the sample to swell free of any restraining load. During saturation, the sample cup 530 is set on a mesh located in the liquid reservoir so that the sample cup 530 is raised slightly above the bottom of the liquid reservoir. The mesh does not inhibit the flow of saline solution into the sample cup 530. A suitable mesh can be obtained as part number 7308 from Eagle Supply and Plastic, having a place of business in Appleton, Wis., U.S.A. Saline does not fully cover the superabsorbent polymer composition particles, as would be evidenced by a perfectly flat saline surface in the test cell. Also, saline depth is not allowed to fall so low that the surface within the cell is defined solely by swollen superabsorbent, rather than saline.

At the end of this period, the plunger 536 and weight 548 assembly is placed on the saturated sample 568 in the sample container 530 and then the sample container 530, plunger 536, weight 548, and sample 568 are removed from the solution. After removal and before being measured, the sample container 530, plunger 536, weight 548, and sample 568 are to remain at rest for about 30 seconds on a suitable flat, large grid non-deformable plate of uniform thickness. The thickness of the saturated sample 568 is determined by again measuring the height from the top of the weight 548 to the bottom of the sample container 530, using the same thickness gauge used previously provided that the zero point is unchanged from the initial height measurement. The sample container 530, plunger 536, weight 548, and sample 568 may be placed on a flat, large grid non-deformable plate of uniform thickness that will prevent liquid in the sample container from being released onto a flat surface due to surface tension. The plate has an overall dimension of 7.6 cm by 7.6 cm, and each grid has a cell size dimension of 1.59 cm long by 1.59 cm wide by 1.12 cm deep. A suitable flat, large grid non-deformable plate material is a parabolic diffuser panel, catalogue number 1624K27, available from McMaster Carr Supply Company, having a place of business in Chicago, Ill., U.S.A., which can then be cut to the proper dimensions. This flat, large mesh non-deformable plate must also be present when measuring the height of the initial empty assembly. The height measurement should be made as soon as practicable after the thickness gauge is engaged. The height measurement obtained from measuring the empty sample container 530, plunger 536, and weight 548 is subtracted from the height measurement obtained after saturating the sample 568. The resulting value is the thickness, or height "H" of the swollen sample.

The permeability measurement is initiated by delivering a flow of the 0.9% saline solution into the sample container 530 with the saturated sample 568, plunger 536, and weight 548 inside. The flow rate of test solution into the container is adjusted to cause saline solution to overflow the top of the cylinder 534 thereby resulting in a consistent head pressure equal to the height of the sample container 530. The test solution may be added by any suitable means that is sufficient to ensure a small, but consistent amount of overflow from the top of the cylinder, such as with a metering pump 604. The overflow liquid is diverted into a separate collection device 601. The quantity of solution passing through the sample 568 versus time is measured gravimetrically using the scale 602 and beaker 603. Data points from the scale 602 are collected every second for at least sixty seconds once the overflow has begun. Data collection may be taken manually or with data collection software. The flow rate, Q, through the swollen sample 568 is determined in units of grams/second (g/s) by a linear least-square fit of fluid passing through the sample 568 (in grams) versus time (in seconds).

Permeability in cm$^2$ is obtained by the following equation:

$$K=[Q*H*\mu]/[A*\rho*P]$$

where K=Permeability (cm$^2$), Q=flow rate (g/sec), H=height of swollen sample (cm), μ=liquid viscosity (poise) (approximately one centipoise for the test solution used with this Test), A=cross-sectional area for liquid flow (28.27 cm$^2$ for the sample container used with this Test), ρ=liquid density (g/cm$^3$) (approximately one g/cm$^3$, for the test solution used with this Test) and P=hydrostatic pressure (dynes/cm$^2$) (nominally approximately 7,797 dynes/cm$^2$). The hydrostatic pressure is calculated from P=ρ*g*h, where ρ=liquid density (g/cm$^3$), g=gravitational acceleration, nominally 981 cm/sec$^2$, and h=fluid height, e.g., 7.95 cm for the Gel Bed Permeability Test described herein.

A minimum of two samples is tested and the results are averaged to determine the gel bed permeability of the sample.

Absorbency Under Load Test (AUL(0.9 psi))

The Absorbency Under Load (AUL) Test measures the ability of the superabsorbent polymer composition particles to absorb a 0.9 weight percent solution of sodium chloride in distilled water at room temperature (test solution) while the material is under a 0.9 psi load. The apparatus for testing AUL consists of:

An AUL assembly including a cylinder, a 4.4 g piston, and a standard 317 gm weight. The components of this assembly are described in additional detail below.

A flat-bottomed square plastic tray that is sufficiently broad to allow the glass frits to lay on the bottom without contact with the tray walls. A plastic tray that is 9" by 9"(22.9 cm×22.9 cm), with a depth of 0.5 to 1" (1.3 cm to 2.5 cm) is commonly used for this test method.

A 12.5 cm diameter sintered glass frit with a 'C' porosity (25-50 microns). This frit is prepared in advance through equilibration in saline (0.9% sodium chloride in distilled water, by weight). In addition to being washed with at least two portions of fresh saline, the frit must be immersed in saline for at least 12 hours prior to AUL measurements.

Whatman Grade 1, 12.5 cm diameter filter paper circles.

A supply of saline (0.9% sodium chloride in distilled water, by weight).

Figure 8:
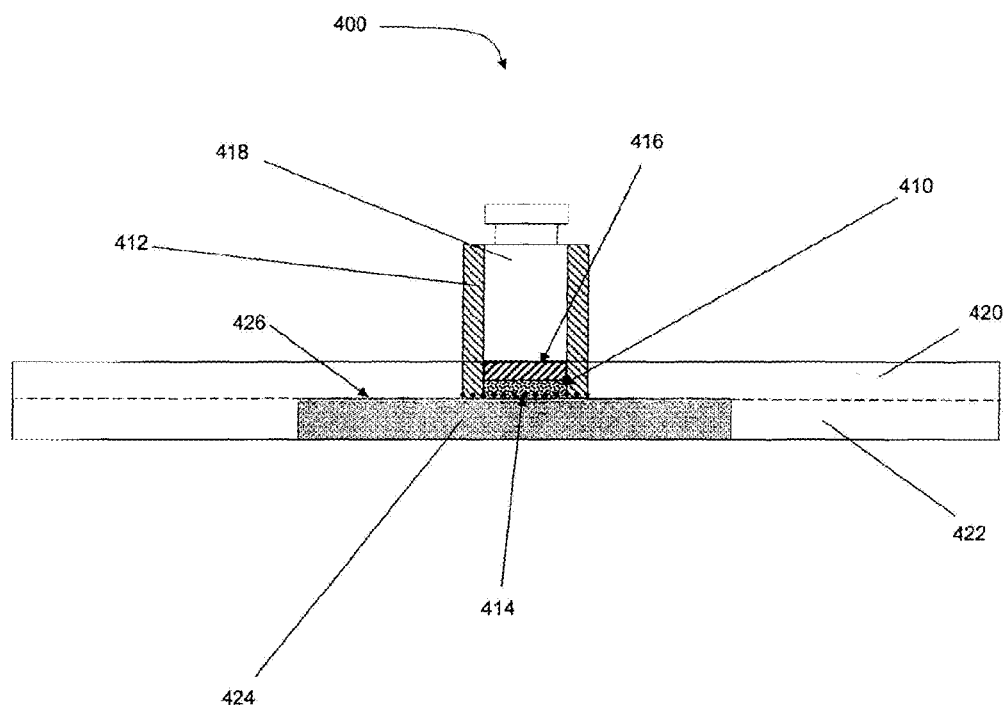
FIG. 8 is a side view of the test apparatus employed for the Absorbency Under Load Test.

Referring to FIG. 8, the cylinder 412 of the AUL assembly 400 used to contain the superabsorbent polymer composition particles 410 is made from one-inch (2.54 cm) inside diameter thermoplastic tubing machined-out slightly to be sure of concentricity. After machining, a 400 mesh stainless steel wire cloth 414 is attached to the bottom of the cylinder 412 by heating the steel wire cloth 414 in a flame until red hot, after which the cylinder 412 is held onto the steel wire cloth until cooled. A soldering iron can be utilized to touch up the seal if unsuccessful or if it breaks. Care must be taken to maintain a flat smooth bottom and not distort the inside of the cylinder 412.

The 4.4 g piston (416) is made from one-inch diameter solid material (e.g., PLEXIGLAS®) and is machined to closely fit without binding in the cylinder 412.

A standard 317 gm weight 418 is used to provide a 62,053 dyne/cm$^2$ (about 0.9 psi) restraining load. The weight is a cylindrical, 1 inch (2.5 cm) diameter, stainless steel weight that is machined to closely fit without binding in the cylinder.

Unless specified otherwise, a sample 410 corresponding to a layer of at least about 300 gsm. (0.16 g) of superabsorbent polymer composition particles is utilized for testing the AUL. The sample 410 is taken from superabsorbent polymer composition particles that are pre-screened through U.S. standard #30 mesh and retained on U.S. std. #50 mesh. The superabsorbent polymer composition particles can be pre-screened with, for example, a RO-TAP® Mechanical Sieve Shaker Model B available from W. S. Tyler, Inc., Mentor Ohio. Sieving is conducted for about 10 minutes.

The inside of the cylinder 412 is wiped with an antistatic cloth prior to placing the superabsorbent polymer composition particles 410 into the cylinder 412.

The desired amount of the sample of sieved superabsorbent polymer composition particles 410 (about 0.16 g) is weighed out on a weigh paper and evenly distributed on the wire cloth 414 at the bottom of the cylinder 412. The weight of the superabsorbent polymer composition particles in the bottom of the cylinder is recorded as 'SA,' for use in the AUL calculation described below. Care is taken to be sure no superabsorbent polymer particles cling to the wall of the cylinder. After carefully placing the 4.4 g piston 412 and 317 g weight 418 on the superabsorbent polymer composition particles 410 in the cylinder 412, the AUL assembly 400 including the cylinder, piston, weight, and superabsorbent polymer composition particles is weighed, and the weight is recorded as weight 'A'.

A sintered glass frit 424 (described above) is placed in the plastic tray 420, with saline 422 added to a level equal to that of the upper surface of the glass frit 424. A single circle of filter paper 426 is placed gently on the glass frit 424, and the AUL assembly 400 with the superabsorbent polymer composition particles 410 is then placed on top of the filter paper 426. The AUL assembly 400 is then allowed to remain on top of the filter paper 426 for a test period of one hour, with attention paid to keeping the saline level in the tray constant. At the end of the one hour test period, the AUL apparatus is then weighed, with this value recorded as weight 'B.'

The AUL(0.9 psi) is calculated as follows:

$$AUL(0.9\ psi) = (B-A)/SA$$

wherein

A=Weight of AUL Unit with dry SAP
B=Weight of AUL Unit with SAP after 60 minutes absorption
SA=Actual SAP weight A minimum of two tests is performed and the results are averaged to determine the AUL value under 0.9 psi load. The samples are tested at about 23° C. and about 50% relative humidity.

Vortex Time

General Description: The vortex test measures the amount of time in seconds required for 2 grams of a superabsorbent polymer composition to close a vortex created by stirring 50 milliliters of saline solution at 600 revolutions per minute on a magnetic stir plate. The time it takes for the vortex to close is an indication of the free swell absorbing rate of the superabsorbent polymer composition.

Equipment & Materials
1. Beaker, 100 milliliter
2. Programmable magnetic stir plate, capable of providing 600 revolutions per minute (such as that commercially available from PMC Industries as Dataplate®. Model #721).
3. Magnetic stir bar without rings, 7.9 millimeters.times.32 millimeters, Teflon™ covered (such as that commercially available from Baxter Diagnostics, under the trade designation S/PRIM. brand single pack round stirring bars with removable pivot ring).
4. Stopwatch
5. Balance, accurate to +/−.0.01 gram
6. Saline solution, 0.87 w/w percent, Blood Bank Saline available from Baxter Diagnostics (considered, herein to be the equivalent of 0.9 weight percent saline)
7. Weighing paper
8. Room with standard condition atmosphere: Temperature=23° C.+/−1° C. and Relative Humidity=50%+/−2%.

Test Procedure
1. Measure 50 g+/−0.01 gram of saline solution into the 100 milliliter beaker.
2. Place the magnetic stir bar into the beaker.
3. Program the magnetic stir plate to 600 revolutions per minute.
4. Place the beaker on the center of the magnetic stir plate such that the magnetic stir bar is activated. The bottom of the vortex should be near the top of the stir bar.
5. Weigh out 2 g+/−0.01 gram of the superabsorbent polymer composition to be tested on weighing paper.
NOTE: The superabsorbent polymer composition is tested as received (i.e. as it would go into an absorbent composite such as those described herein). No screening to a specific particle size is done, though the particle size is known to have an effect on this test.
6. While the saline solution is being stirred, quickly pour the superabsorbent polymer composition to be tested into the saline solution and start the stopwatch. The superabsorbent polymer composition to be tested should be added to the saline solution between the center of the vortex and the side of the beaker.
7. Stop the stopwatch when the surface of the saline solution becomes flat and record the time.
8. The time, recorded in seconds, is reported as the Vortex Time.

EXAMPLES

The following comparative examples and examples, and preproduct therefore, are provided to illustrate the invention and do not limit the scope of the claims. Unless otherwise stated all parts, and percentages are by weight.

SAP Preproduct

Into a polyethylene container equipped with an agitator and cooling coils was added 482 grams of 50% NaOH and 821 grams of distilled water and cooled to 20° C. 207 grams of glacial acrylic acid was then added to the caustic solution and the solution again cooled to 20° C. Specific amount of internal crosslinkers in accordance with Tables 2 to 3 for Comparative Examples 1 to 7 and Examples 1 to 18, and 413 grams of glacial acrylic acid were added to the first solution, followed by cooling to 4-6° C. Nitrogen was bubbled through the monomer solution for about 10 minutes. The cooling coils were removed from the container. To the monomer solution was added 20 g of 1% by weight of $H_2O_2$ aqueous solution, 30 g of 2 wt % aqueous sodium persulfate solution, and 18 g of 0.5 wt % aqueous sodium erythorbate solution to initiate polymerization reaction. The agitator was stopped and the initiated monomer was allowed to polymerize for 20 minutes. The resulting hydrogel was chopped and extruded with a Hobart 4M6 commercial extruder, followed by drying in a Procter & Schwartz Model 062 forced air oven at 175° C. for 12 minutes with up flow and 6 minutes with down flow air on a 20 in×40 in perforated metal tray to a final product moisture level of less than 5 wt %. The dried material was coarseground in a Prodeva Model 315-S crusher, milled in an MPI 666-F three-stage roller mill and sieved with a Minox MTS 600DS3V to remove particles greater than 850 μm and smaller than 150 μm.

Comparative Examples 1 to 6

In accordance with Table 2 for Comparative Examples 1 to 6, crosslinkers and silicon compounds were added into the monomer solution in the SAP Preproduct to prepare superabsorbent polymers.

Comparative examples 1 to 5 demonstrate that silane or silicate compounds without carbon-carbon double bonds are not effective internal crosslinkers for polyacrylate based superabsorbent polymers. In addition, CRC Increase was not observed in these comparative examples.

Comparative example 6 demonstrates that 3-trimethoxysily propyl methacrylate is an effective crosslinker for superabsorbent polymers. But CRC Increase was not observed in this case. The crosslinking formed by 3-trimethoxysily propyl methacrylate probably is stable over the time. The chemical structure of 3-trimethoxysily propyl methacrylate is shown below.

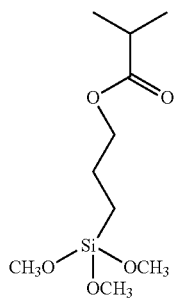

TABLE 2

| Sample | Second Internal crosslinker | Silane Crosslinker | CRC(rt, 0.5 hr) | CRC(rt, 16 hr) |
|---|---|---|---|---|
| CE 1 | 0.4% of A* | none | 47.3 | 47.8 |
| CE 2 | 0.4% of A | 1% sodium methylsilicate | 48.9 | 50.2 |
| CE 3 | 0.4% of A | 1% of methyltrimethoxy silane | 49.7 | 50.8 |
| CE 4 | 0.4% of A | 1% of tetraethoxy orthosilicate | 51.9 | 52.4 |
| CE 5 | 0.4% of A | 1% of tetraacetoxysilicate | 51.8 | 52.4 |
| CE 6 | 0.4% of A | 0.5% of 3-trimethoxysily propyl methacrylate | 25.2 | 26.0 |

*Crosslinker A: polyethylene glycol monoallylether acrylate,

Comparative Example 7 and Examples 1 to 13

In accordance with Table 3 for Comparative Example 7 and Examples 1 to 13, conventional crosslinker(s) and/or silicon crosslinker(s) were added into the monomer solution of the SAP Preproduct to prepare superabsorbent polymers.

The results in Table 3 indicate that the CRC of samples Ex 1 to 13 increases over the time either at room temperature or body temperature. In addition, CRC increases with the increase of the testing temperature. Furthermore, CRC increases faster at body temperature than at room temperature.

In comparison, sample CE 7 which comprises only conventional internal crosslinker shows essentially constant CRC over the time or at different temperatures.

TABLE 3

| Ex | Second Internal Crosslinker | Silane or siloxane crosslinker | CRC (rt, 0.5 hr) | CRC (rt, 5 hrs) | CRC (bt, 0.5 hr) | CRC (bt, 5 hrs) |
|---|---|---|---|---|---|---|
| CE 7 | 0.5% of A*, and 0.25% of C*** | none | 43 | 43.9 | 43.4 | 42.7 |
| Ex 1 | none | 1% of Dynasylan ® 6490 | 27.1 | 41.3 | 39.1 | 78.3 |
| Ex 2 | 0.4% of A | 1% vinyltriisopropenoxy silane | 30.5 | 37.9 | 36.2 | 47.7 |
| Ex 3 | 0.4% of A | 1% vinyltriacetoxy silane | 27.4 | 34.7 | 33.9 | 45.2 |
| Ex 4 | 0.4% of A | 1% vinyltrimethoxy silane | 20.6 | 27.2 | 26.2 | 40.9 |
| Ex 5 | 0.4% of A | 1% vinyltriethoxy silane | 20.5 | 28.8 | 27.8 | 43.5 |
| Ex 6 | 0.4% of A | 1% diethoxymethylvinyl silane | 40.4 | 50.1 | 49.3 | 52.3 |
| Ex 7 | 0.4% of A | 1% of Dynasylan ® 6498 | 39.6 | 45.2 | 44.6 | 49.4 |
| Ex 8 | 0.4% of A | 0.5% of Dynasylan ® 6490 | 26.1 | 33.7 | 32.6 | 44.4 |
| Ex 9 | 0.4% of A | 0.375% of Dynasylan ® 6490 | 30.2 | 35.5 | 33.5 | 43.1 |
| Ex 10 | 0.2% of A, and 0.1% of B** | 0.5% of Dynasylan ® 6490 | 26.1 | 33.6 | 32.4 | 41.3 |
| Ex 11 | 0.2% of A, and 0.1% of C | 0.25% of Dynasylan ® 6490 | 41.4 | 48.2 | 46.2 | 56.3 |
| Ex 12 | 0.2% of A, and 0.1% of C | 0.375% of Dynasylan ® 6490 | 35.2 | 42.2 | 40.2 | 52.2 |

TABLE 3-continued

| Ex | Second Internal Crosslinker | Silane or siloxane crosslinker | CRC (rt, 0.5 hr) | CRC (rt, 5 hrs) | CRC (bt, 0.5 hr) | CRC (bt, 5 hrs) |
|---|---|---|---|---|---|---|
| Ex 13 | 0.2% of A, and 0.1% of C | 0.5% of Dynasylan® 6490 | 31.1 | 38.9 | 35.3 | 48.6 |

*Crosslinker A: polyethylene glycol monoallylether acrylate,
**Crosslinker B: ethoxylated trimethylol propane triacrylate (SARTOMER® 454 product)
***Crosslinker C: polyethylene glycol 300 diacrylate Comparative Example 8

100 g of the product obtained from Comparative Example 7 was blended uniformly with 0.5% of Sipernat® 22s (commercially available from Evonik-Degussa Corporation), followed by the uniform spray application of a solution containing 1 wt % ethylene carbonate and 4 wt % of water using a finely atomized spray while the SAP particles are fluidized in air. The coated material was then heated at 185° C. for 55 minutes at in a convection oven. The product was cooled and sieved to remove particles greater than 850 µm and smaller than 150 µm.

Example 14

100 g of the product obtained from Example 12 was blended uniformly with 0.5% of Sipernat® 22s, followed by the uniform spray application of a solution containing 1 wt % ethylene carbonate and 4 wt % of water using a finely atomized spray while the SAP particles are fluidized in air. The coated material was then heated at 185° C. for 55 minutes at in a convection oven. The product was cooled and sieved to remove particles greater than 850 µm and smaller than 150 µm.

Example 15

Similar to Example 14 except the product from Example 13 was used as the base polymer and the coated material was heated for 40 minutes at 185° C.

Example 16

100 g of the product obtained from Example 12 was blended uniformly with 0.5% of Sipernat® 22s, followed by the uniform spray application of a solution containing 1 wt % ethylene carbonate, 200 ppm of maleated polypropylene, and 4 wt % of water using a finely atomized spray while the SAP particles are fluidized in air. The coated material was then heated at 185° C. for 55 minutes at in a convection oven. The product was cooled and sieved to remove particles greater than 850 µm and smaller than 150 µm.

Example 17

100 g of the product obtained from Example 12 was blended uniformly with 0.5% of Sipernat® 22s, followed by the uniform spray application of a solution containing 1 wt % ethylene carbonate, 200 ppm of maleated polypropylene, 0.25% of aluminum phosphate, and 4 wt % of water using a finely atomized spray while the SAP particles are fluidized in air. The coated material was then heated at 185° C. for 55 minutes at in a convection oven. The product was cooled and sieved to remove particles greater than 850 µm and smaller than 150 µm.

Example 18

100 g of the product obtained from Example 17 was coated with a solution containing 0.2 wt % of polyvinylamine (Lupamin® 9025), 0.1% of PEG-8000, and 3 wt % of water using a finely atomized spray while the SAP particles are fluidized in air. The coated material was relaxed at room temperature for overnight and sieved to remove particles greater than 850 µm and smaller than 150 µm.

Example 19

100 g of the product obtained from Example 12 was coated with a solution containing 1 wt % ethylene carbonate, 1% of aluminum sulfate, 200 ppm of maleated polypropylene, and 4 wt % of water using a finely atomized spray while the SAP particles are fluidized in air. The coated material was then heated at 185° C. for 55 minutes at in a convection oven. The product was cooled and sieved to remove particles greater than 850 µm and smaller than 150 µm.

Table 4 summarizes the results for surface crosslinked and surface treated samples. As we can see from Table 4, the CRC(rt,0.5 hr), CRC(rt,5 hr), CRC(bt,0.5 hr), and CRC(bt,5 hr) of samples Ex 14 to 19 increases over the time either at room temperature or body temperature. In addition, CRC increases with the increase of the testing temperature. Furthermore, CRC increases faster at body temperature than at room temperature. In comparison, sample CE 8 which comprises only conventional internal crosslinker shows essentially constant CRC over the time or at different temperatures.

TABLE 4

| Ex | CRC (rt, 0.5 hr) | CRC (rt, 5 hr) | CRC (bt, 0.5 hrs) | CRC (bt, 5 hrs) | AUL (0.9 psi) | GBP |
|---|---|---|---|---|---|---|
| CE 8 | 35.5 | 36.9 | 36.5 | 35.9 | 12.9 | 23 |
| Ex 14 | 29.0 | 34.3 | 33.5 | 41.2 | 17.3 | 54 |
| Ex 15 | 27.9 | 34.5 | 33 | 41.9 | 15.8 | 49 |
| Ex 16 | 26.8 | 30.5 | 30.5 | 34.9 | 19.2 | 90 |
| Ex 17 | 26.3 | 30.2 | 29.9 | 34.8 | 18.9 | 100 |
| Ex 18 | 25.6 | 29.7 | 29.2 | 34.1 | 18.4 | 118 |
| Ex 19 | 27.1 | 31.2 | 31.2 | 36.5 | 19.9 | 69 |

Table 5 shows the values of the CRCI, CRCIR, and vortex time for CE7-8 and examples 1-19.

TABLE 5

| Ex | CRCI(rt) (g/g) | CRCI(bt) (g/g) | CRCIR(rt) (g/g/hour) | CRCIR(bt) (g/g/hour) | Vortex Time (sec) |
|---|---|---|---|---|---|
| CE 7 | 0.9 | −0.3 | 0.20 | −0.16 | 87 |
| CE 8 | 1.4 | 0.4 | 0.31 | −0.13 | 85 |
| Ex 1 | 14.2 | 51.2 | 3.15 | 8.70 | 105 |
| Ex 2 | 7.4 | 17.2 | 1.65 | 2.56 | 115 |
| Ex 3 | 7.3 | 17.8 | 1.62 | 2.53 | n/a |

TABLE 5-continued

| Ex | CRCI(rt) (g/g) | CRCI(bt) (g/g) | CRCIR(rt) (g/g/hour) | CRCIR(bt) (g/g/hour) | Vortex Time (sec) |
|---|---|---|---|---|---|
| Ex 4 | 6.6 | 20.3 | 1.47 | 3.27 | n/a |
| Ex 5 | 8.3 | 23.0 | 1.84 | 3.49 | n/a |
| Ex 6 | 9.7 | 11.9 | 2.16 | 0.66 | 97 |
| Ex 7 | 5.6 | 9.8 | 1.25 | 1.06 | 85 |
| Ex 8 | 7.6 | 18.3 | 1.68 | 2.61 | 120 |
| Ex 9 | 5.3 | 12.9 | 1.17 | 2.14 | 85 |
| Ex 10 | 7.5 | 15.2 | 1.66 | 1.99 | 112 |
| Ex 11 | 6.8 | 14.9 | 1.51 | 2.24 | 84 |
| Ex 12 | 7.0 | 17.0 | 1.56 | 2.67 | 91 |
| Ex 13 | 7.8 | 17.5 | 1.73 | 2.96 | 113 |
| Ex 14 | 5.3 | 12.2 | 1.18 | 1.71 | 96 |
| Ex 15 | 6.6 | 14.0 | 1.47 | 1.98 | 107 |
| Ex 16 | 3.8 | 8.1 | 0.84 | 0.99 | 95 |
| Ex 17 | 3.9 | 8.5 | 0.87 | 1.09 | 103 |
| Ex 18 | 4.1 | 8.4 | 0.90 | 1.07 | 87 |
| Ex 19 | 4.1 | 9.4 | 0.92 | 1.18 | 85 |

As shown in Table 5, the CRCIR(rt) and CRCIR(bt) of Examples 1 to 19 are higher than 0.4 g/g/hour, while the increase rates of Comparative examples 7 and 8 are lower than 0.4 g/g/hour. As shown in Table 5, particulate superabsorbent polymer compositions of the present invention have Vortex times comparable to conventional SAP compositions.

Example 20

To further illustrate that the present capacity increase SAP compositions having have an improved ability to absorb, retain and distribute liquids in absorbent articles, laboratory diaper cores containing the present capacity increase SAP compositions were prepared and compared to laboratory diaper cores containing a conventional SAP. In particular, the following the diaper cores were prepared:
Core A—60% of conventional SAP (as in CE 8), and 40% fluff pulp, by weight,
Core B—60% of capacity increase SAP (as in Ex 14), and 40% fluff pulp, by weight Handsheets (laboratory diaper cores) were prepared using standard airforming handsheet equipment. The resulting handsheet composites had dimensions of 25.4 cm wide by 43.2 cm long.

The handsheets were produced with the following procedure. A sheet of the forming tissue was placed on the bottom of the former. Then, the superabsorbent polymer composition and the fluff were each divided into about equal portions (i.e. 6 portions of fluff and 5 portions of particulate materials). Each fluff portion and particulate materials portion was alternatively introduced into the top of the former, allowing the compressed air to mix the fluff and particulate materials while the vacuum drew the material through the forming chamber and onto the forming tissue. This process was continued until the last portion of fluff was consumed, forming a substantially uniform distribution of fluff and particulate materials. This yielded absorbent composites which had a basis weight 500 gsm. Following web formation, another layer of the above forming tissue was placed on top of the formed composite. The resulting handsheet composite was compressed to achieve the desired density of approximately 0.26 g/cc prior to testing, using for example a CARVER PRESS model #4531 (available from Carver, Inc., having a place of business in Wabash, Ind. U.S.A.). Following handsheet preparation and densification, samples were cut to 7.6 cm×7.6 cm circles for core testing.

Fluid Intake as used in Table 6 was tested according to the Fluid Intake Evaluation Test described in U.S. Pat. No. 7,073,373 and Core Retention Capacity as used in Table 6 was tested according to the Liquid Saturation Retention Capacity Test described in U.S. Pat. No. 7,073,373, except the diaper cores were soaked in the test liquid at 37° C. for 5 hours. Table 6 contains the test results. The Fluid Intake Evaluation Test including FIGS. 4 and 5, and the Liquid Saturation Retention Capacity Test including FIG. 3, as set forth in U.S. Pat. No. 7,073,373, are incorporated by reference into the present application.

TABLE 6

| Code | SAP | Insult amount (g) | 1st Fluid Intake Time (sec) | 2nd Fluid Intake Time (sec) | 3rd Fluid Intake Time (sec) | 4th Fluid Intake Time (sec) | Core Retention Capacity (g/g) |
|---|---|---|---|---|---|---|---|
| Code A | CE 8 | 16.0 | 20.8 | 12.3 | 24.2 | 44.1 | 23.8 |
| Code B | Ex 14 | 16.0 | 19.3 | 9.8 | 17.2 | 32.4 | 25.6 |

The data presented in Table 6 demonstrate that a diaper core of the present invention shows an improved fluid intake time and an increased core retention capacity. The practical result of these improved properties is a core having an improved ability to prevent leakage in gush situations and maintain dryness.

Notwithstanding that the numerical ranges and parameters setting forth the broad scope of the invention are approximations, the numerical values set forth in the specific examples are reported as precisely as possible. Other than in the operating examples, or where otherwise indicated, all numbers expressing quantities of ingredients, reaction conditions, and so forth used in the specification and claims are to be understood as being modified in all instances by the term "about." Any numerical value, however, inherently contain certain errors necessarily resulting from the standard deviation found in their respective testing measurements.

What is claimed is:

1. An absorbent article comprising: (a) a liquid pervious topsheet; (b) a liquid impervious backsheet; (c) a core positioned between (a) and (b), said core comprising about 10% to 100% by weight of a particulate superabsorbent polymer and 0% to about 90% by weight of hydrophilic fiber material; (d) optionally a tissue layer positioned directly above and below said core (c); and (e) an acquisition layer positioned between (a) and (c); wherein the particulate superabsorbent polymer comprises a monomer selected from an ethylenically unsaturated carboxylic acid, ethylenically unsaturated carboxylic acid anhydride, salts or derivatives thereof, and an internal crosslinker agent wherein the internal crosslinker agent comprises a silane compound comprising at least one vinyl group or allyl group and at least one Si—O bond wherein the vinyl group or allyl group is directly attached to a silicon atom, wherein the superabsorbent polymer has a Centrifuge Retention Capacity Increase of 2 g/g or more based on $$\text{CRC Increase} = \text{CRC}(rt, 5\ hr) - \text{CRC}(rt, 0.5\ hr)$$

and wherein CRC Increase measures the increase in the CRC that occurs and is calculated as the difference between the second CRC and first CRC and rt refers to room temperature.

2. The absorbent article of claim 1 wherein the particulate superabsorbent polymer has a Centrifuge Retention Capacity Increase of from about 2 g/g to about 50 g/g.

3. The absorbent article claim 1 wherein said silane compound is selected from vinyltriisopropenoxy silane, vinyltriacetoxysilane, vinyltrimethoxysilane, vinyltriethoxysilane, diethoxymethylvinyl silane, and polysiloxane comprising at least two vinyl groups.

4. The absorbent article of claim 1 further comprising a second internal crosslinker.

5. The absorbent article of claim 4 wherein the second internal crosslinker is selected from polyethylene glycol monoallyl ether acrylate, ethoxylated trimethylol propane triacrylate, or polyethylene glycol diacrylate.

6. The absorbent article of claim 1 wherein the particulate superabsorbent polymer has a Centrifuge Retention Capacity Increase of from about 2 g/g to about 40 g/g.

7. The absorbent article of claim 1 wherein the particulate superabsorbent polymer has a Centrifuge Retention Capacity Increase Rate of from about 0.4 g/g/hr to about 10 g/g/hr based on $$\text{CRC Increase Rate} = \text{CRC}(rt, 5\ hr) - \text{CRC}(rt, 0.5\ hr)$$

wherein the CRC Increase Rate measures the ability of the particulate superabsorbent polymer to gain additional CRC over the time when contacted with the liquid.

8. The absorbent article of claim 1 wherein the particulate superabsorbent polymer has a Centrifuge Retention Capacity measured at body temperature (CRC(bt)) and a Centrifuge Retention Capacity measured at room temperature (CRC(rt)) wherein CRC(bt) and CRC(rt) have the same testing time and CRC(bt) is about 2 g/g to 20 g/g higher than CRC(rt).

* * * * *